(12) United States Patent
Seo et al.

(10) Patent No.: US 11,529,066 B1
(45) Date of Patent: Dec. 20, 2022

(54) ANTENNA DEVICE FOR MEASURING BIOMETRIC INFORMATION BY USING DARK MODE EXCITATION

(71) Applicant: SB Solutions Inc., Ulsan (KR)

(72) Inventors: Seungup Seo, Ulsan (KR); Namhwan Sung, Ulsan (KR); Hae Dong Lee, Ulsan (KR); Seong Mun Kim, Ulsan (KR); Ji Woong Song, Ulsan (KR); Jagannath Malik, Ulsan (KR)

(73) Assignee: SB SOLUTIONS INC., Ulsan (KR)

( * ) Notice: Subject to any disclaimer, the term of this patent is extended or adjusted under 35 U.S.C. 154(b) by 0 days.

(21) Appl. No.: 17/535,363

(22) Filed: Nov. 24, 2021

(30) Foreign Application Priority Data

Aug. 13, 2021 (KR) ........................ 10-2021-0107640

(51) Int. Cl.
  *A61B 5/05* (2021.01)
  *A61B 5/145* (2006.01)
  *H01Q 9/16* (2006.01)
  *H01Q 7/00* (2006.01)

(52) U.S. Cl.
  CPC ............ *A61B 5/05* (2013.01); *A61B 5/14503* (2013.01); *A61B 5/14532* (2013.01); *H01Q 7/00* (2013.01); *H01Q 9/16* (2013.01); *A61B 2562/0223* (2013.01)

(58) Field of Classification Search
  CPC ... A61B 5/05; A61B 5/14503; A61B 5/14532; A61B 5/1455
  See application file for complete search history.

(56) References Cited

U.S. PATENT DOCUMENTS

| | | |
|---|---|---|
| 5,945,959 A | 8/1999 | Tanidokoro et al. |
| 6,015,387 A | 1/2000 | Schwartz et al. |
| 2006/0161225 A1 | 7/2006 | Sormann et al. |
| 2017/0271926 A1 | 9/2017 | Plekhanov et al. |
| 2019/0254576 A1* | 8/2019 | Bien ..................... A61B 5/742 |

FOREIGN PATENT DOCUMENTS

| | | |
|---|---|---|
| KR | 10-2014-0067355 A | 7/2020 |
| KR | 10-2185556 B1 | 12/2020 |

OTHER PUBLICATIONS

International Search Report dated May 13, 2022, issued in corresponding International Patent Application No. PCT/KR2021/013081, filed Aug. 13, 2021, 3 pages.

* cited by examiner

*Primary Examiner* — Marjan Fardanesh
(74) *Attorney, Agent, or Firm* — Christensen O'Connor Johnson Kindness PLLC

(57) ABSTRACT

Disclosed is an antenna device for measuring biometric information by using dark mode excitation. The antenna device according to an embodiment may include a conducting wire forming a loop. A current may be induced into the loop through an interaction with a magnetic field generated by an antenna connected to a power source. Information on an analyte may be sensed using a magnetic field formed based on the current induced into the loop.

15 Claims, 35 Drawing Sheets and may include contents which do not form a part of a conventional technology and may not include contents which may be presented to those skilled in the art through a conventional technology.

ANTENNA DEVICE FOR MEASURING BIOMETRIC INFORMATION BY USING DARK MODE EXCITATION

CROSS-REFERENCES TO RELATED APPLICATIONS

This application is based on and claims priority under 35 U.S.C. 119 to Korean Patent Application No. 10-2021-0107640, filed on Aug. 13, 2021 in the Korean intellectual property office, the disclosures of which are herein incorporated by reference in their entireties.

TECHNICAL FIELD

The following description relates to an antenna device for measuring biometric information by using dark mode excitation.

BACKGROUND OF THE DISCLOSURE

Cases in which adult-onset diseases, such as diabetes, hyperlipidemia and thrombosis, are increased continue to increase. Such diseases need to be periodically measured using various bio sensors because it is important to continuously monitor and manage the diseases. A common type of a bio sensor is a method of injecting, into a test strip, blood gathered from a finger and then quantizing an output signal by using an electrochemical method or a photometry method. Such an approach method causes a user a lot of pain because blood needs to be gathered every time.

For example, in order to manage diabetes of hundreds of millions of people worldwide, the most basic thing is to measure blood glucose. Accordingly, a blood glucose measuring device is an important diagnostic device inevitably necessary for a diabetic. Various blood glucose measuring devices are recently developed, but the most frequently used method is a method of gathering blood by pricking a finger and then directly measuring a concentration of glucose within the blood. An invasive test includes a method of measuring blood glucose through the recognition of an external reader after measuring the blood glucose for a given time by penetrating an invasive sensor into the skin.

In contrast, a non-invasive test includes a method using a light-emitting diode (LED)-photo diode (PD), etc. However, the non-invasive test has low accuracy due to an environmental factor, such as sweat or a temperature, an alien substance, etc. because the LED-PD is attached to the skin.

The aforementioned information is to merely help understanding, and may include contents which do not form a part of a conventional technology and may not include contents which may be presented to those skilled in the art through a conventional technology.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

Embodiments of the present disclosure provides an antenna device for measuring biometric information by using dark mode excitation and an implant device for measuring biometric information by using the antenna device.

In an embodiment, there is provided an antenna device including a conducting wire forming a loop, wherein a current is induced into the loop through an interaction with a magnetic field generated by an antenna connected to a power source and information on an analyte is sensed using a magnetic field formed based on the current induced into the loop.

According to an aspect, the conducting wire may form the loop in a way to have or generate an electric quadrupole moment.

According to another aspect, the conducting wire may form the loop so that a cross-shaped loop is included.

According to still another aspect, the loop may have a length corresponding to half of a wavelength corresponding to a frequency of a supplied feeding signal.

According to still another aspect, the antenna connected to the power source may include a dipole antenna. The current may be induced into the loop through an interaction between the loop and a magnetic field generated by an electric dipole moment of the dipole antenna.

According to still another aspect, the antenna connected to the power source may include a loop antenna.

According to still another aspect, the antenna connected to the power source may include a loop antenna using coplanar waveguide (CPW) feeding.

According to still another aspect, the loop may include a parasitic loop connected to a power source different from the power source so that a current is induced in a direction opposite to a direction of a current flowing into the antenna connected to the power source.

According to still another aspect, the antenna device may further include an antenna connected to the power source.

According to still another aspect, the antenna device may be included in an implant device inserted into a body having a target analyte. The antenna connected to the power source may be included in an external device disposed outside the body having the target analyte. The external device may be implemented to radiate a magnetic field to the implant device inserted into the body having the target analyte through the antenna connected to the power source.

In an embodiment, there is provided an implant device including an antenna device comprising a conducting wire forming a loop, wherein the implant device is inserted into a body having a target analyte, a current is induced into the loop through an interaction with a magnetic field generated by an antenna connected to a power source, and information on an analyte within the body is sensed using a magnetic field formed based on the current induced into the loop.

According to embodiments, there can provided the antenna device for measuring biometric information by using dark mode excitation and the implant device for measuring biometric information by using the antenna device.

DESCRIPTION OF THE DRAWINGS

The foregoing aspects and many of the attendant advantages of this disclosure will become more readily appreciated as the same become better understood by reference to the following detailed description, when taken in conjunction with the accompanying drawings, wherein.

DETAILED DESCRIPTION

Figure 1:
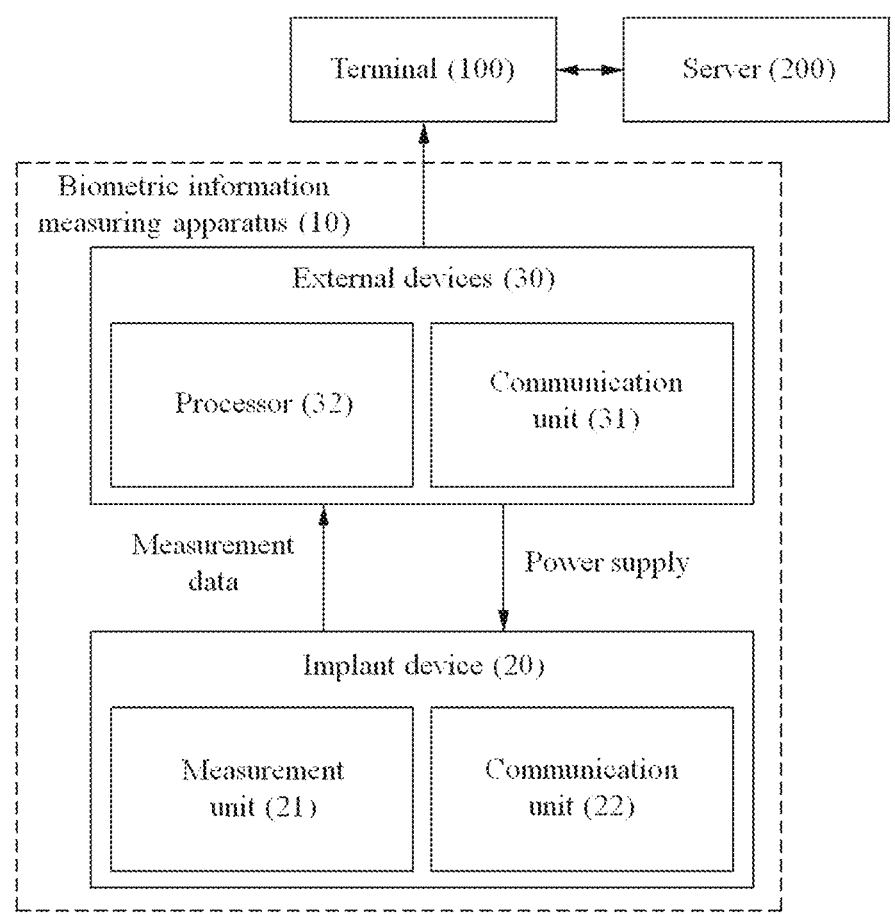
FIG. 1 is a block diagram illustrating an example of a biometric information measuring apparatus according to an embodiment of the present disclosure.

While illustrative embodiments have been illustrated and described, it will be appreciated that various changes can be made therein without departing from the spirit and scope of the disclosure.

Hereinafter, embodiments are described in detail with reference to the accompanying drawings. However, the embodiments may be changed in various ways, and the scope of right of this patent application is not limited or restricted by such embodiments. It is to be understood that all changes, equivalents and substitutions of the embodiments are included in the claims of the application.

Terms used in embodiments are merely used for a description purpose and should not be interpreted as intending to restrict the present disclosure. An expression of the singular number includes an expression of the plural number unless clearly defined otherwise in the context. In this specification, it should be understood that a term, such as "include" or "have", is intended to designate the presence of a characteristic, a number, a step, an operation, a component, a part or a combination of them described in the specification, and does not exclude the existence or possible addition of one or more other characteristics, numbers, steps, operations, components, parts, or combinations of them in advance.

All terms used herein, including technical or scientific terms, have the same meanings as those commonly understood by a person having ordinary knowledge in the art to which an embodiment pertains, unless defined otherwise in the specification. Terms, such as those commonly used and defined in dictionaries, should be construed as having the same meanings as those in the context of a related technology, and are not construed as being ideal or excessively formal unless explicitly defined otherwise in the specification.

Furthermore, in describing the present disclosure with reference to the accompanying drawings, the same component is assigned the same reference numeral regardless of its reference numeral, and a redundant description thereof is omitted. In describing an embodiment, a detailed description of a related known art will be omitted if it is deemed to make the subject matter of the embodiment unnecessarily vague.

Furthermore, in describing elements of an embodiment, terms, such as a first, a second, A, B, (a), and (b), may be used. Such terms are used only to distinguish one component from the other component, and the essence, order, or sequence of a corresponding component is not limited by the terms. When it is said that one component is "connected", "combined", or "coupled" to the other component, the one component may be directly connected or coupled to the other component, but it should also be understood that a third component may be "connected", "combined", or "coupled" between the two components.

A component included in any one embodiment and a component including a common function are described using the same name in another embodiment. Unless described otherwise, a description written in any one embodiment may be applied to another embodiment, and a detailed description in a redundant range is omitted.

According to an embodiment, there is provided a technique relating to an in-body bio sensor capable of semi-permanently measuring blood glucose. The in-body bio sensor may also be called an invasive type bio sensor, an insertion type bio sensor, or an implant type bio sensor. The in-body bio sensor may be a sensor for sensing a target analyte by using an electromagnetic wave. For example, the in-body bio sensor may measure biometric information associated with a target analyte. Hereinafter, the target analyte is a material associated with a living body, and may also be called a living body material or an analyte. For reference, in this specification, the target analyte is chiefly described as blood glucose, but the present disclosure is not limited thereto. The biometric information is information related to a bio component of a target, and may include a concentration of a target analyte or a numerical value, for example. If a target analyte is blood glucose, biometric information may include a blood glucose numerical value.

The in-body bio sensor may measure a bio parameter (hereinafter referred to as a "parameter") associated with a bio component, and may determine biometric information from the measured parameter. In this specification, a parameter may indicate a circuit network parameter used to interpret a bio sensor and/or a bio sensing system, and is described by chiefly taking a scattering parameter as an example, for convenience of description, but the present disclosure is not limited thereto. For example, an admittance parameter, an impedance parameter, a hybrid parameter, a transmission parameter, etc. may be used as the parameter. A permeability coefficient and a reflection coefficient may be used as the scattering parameter. For reference, a resonant frequency calculated from a scattering parameter may be related to a concentration of a target analyte. The in-body bio sensor may predict blood glucose by sensing a change in the permeability coefficient and/or the reflection coefficient.

The in-body bio sensor may include a resonator assembly (e.g., an antenna). Hereinafter, an example in which the resonator assembly is an antenna is chiefly described. A resonant frequency of an antenna may be represented as a capacitance component and an inductance component as in Equation 1.

$$f = \frac{1}{2\pi\sqrt{LC}}$$ [Equation 1]

In Equation 1, f may indicate the resonant frequency of the antenna included in the in-body bio sensor using an electromagnetic wave. L may indicate inductance of the antenna. C may indicate capacitance of the antenna. The capacitance C of the antenna may be proportional to a relative dielectric constant $\varepsilon_r$ as in Equation 2 below.

$$C \propto \varepsilon_r$$ [Equation 2]

The relative dielectric constant $\varepsilon_r$ of the antenna may be influenced by a concentration of a surrounding target analyte. For example, when an electromagnetic wave passes through a material having a given dielectric constant, amplitude and a phase of the electromagnetic wave may be changed due to the reflection and scattering of the electromagnetic wave. The relative dielectric constant $\varepsilon_r$ may also vary because a degree of the reflection and/or scattering of the electromagnetic wave is different depending on a concentration of a target analyte around the in-body bio sensor. It may be interpreted that bio capacitance is formed between the in-body bio sensor and the target analyte due to a fringing field attributable to the electromagnetic wave radiated by the in-body bio sensor including an antenna. A resonant frequency of the antenna also varies because the relative dielectric constant $\varepsilon_r$ of the antenna varies depending on a change in the analyte concentration. In other words, the analyte concentration may correspond to the resonant frequency.

The in-body bio sensor according to an embodiment may radiate an electromagnetic wave while sweeping a frequency, and may measure a scattering parameter according to the radiated electromagnetic wave. The in-body bio sensor may determine a resonant frequency from the measured scattering parameter, and may estimate a blood glucose numerical value corresponding to the determined resonant frequency. The in-body bio sensor may be inserted into a subcutaneous layer, and may predict blood glucose diffused from a blood vessel to an interstitial fluid.

The in-body bio sensor may estimate biometric information by determining a frequency shift degree of a resonant frequency. In order to more accurately measure the resonant frequency, a quality factor may be maximized. Hereinafter, an antenna structure having an improved quality factor in an antenna device used in a bio sensor using an electromagnetic wave is described.

FIG. 1 is a block diagram illustrating an example of a biometric information measuring apparatus according to an embodiment of the present disclosure. The biometric information measuring apparatus 10 according to the present embodiment may include an implant device 20 inserted into the body having a target analyte whose biometric information (e.g., an analyte concentration, such as blood glucose or oxygen saturation) is to be measured and an external devices 30 disposed in the exterior of the target analyte at a location corresponding to a location of the implant device 20. The target analyte may be a human being or an animal. In this case, the implant device 20 may correspond to the aforementioned in-body bio sensor.

The external device 30 is a sensor attached to the outside of the body having the target analyte or worn by the target analyte, and may be fixed to the exterior of the target analyte by using various methods, such as a bending method and an adhesive method. The external device 30 may include a communication unit 31, and the external devices 30 may be paired through the communication units 31 or may provide biometric information to a preset terminal 100.

According to an embodiment, the external device 30 may also provide biometric information itself to the terminal 100, may perform a variety of types of analysis on the biometric information, and may provide the terminal 100 with the results of the analysis, a warning, etc. If the external device 30 provides biometric information itself to the terminal 100, the terminal 100 may perform a variety of types of analysis on the biometric information. Means for analyzing such biometric information may be easily selected by a practicer.

Furthermore, the external devices 30 can secure measurement accuracy and measurement continuity by blocking a performance change attributable to an external environment. The external devices 30 can improve accuracy by securing complementary data with the implant device 20.

The implant device 20 may be inserted into the body having a target analyte. For example, the implant device 20 does not directly come into contact with blood or is not disposed within a blood vessel, but may be disposed in an area other than a blood vessel at a given depth from the skin of a target. In other words, the implant device 20 is preferably disposed in a hypodermic area between the skin and the blood vessel.

The implant device 20 may radiate an electromagnetic wave having a specific frequency, and may measure a concentration of an analyte by measuring a signal reflected by the analyte around a sensor. For example, if blood glucose is to be measured, the implant device 20 may radiate an electromagnetic wave having a specific frequency, and may measure biometric information, such as blood glucose, by measuring a signal reflected by an analyte, such as glucose around a sensor.

The external devices 30 may be disposed in the exterior of a target analyte at a location corresponding to a location where the implant device 20 is disposed, supply power to the implant device 20, and may receive measurement data (e.g., the aforementioned biometric information) measured by the implant device 20.

When a concentration (e.g., a blood glucose numerical value) of a target analyte within a blood vessel of the target analyte is changed, a concentration of the analyte in a hypodermic area may be changed. In this case, a dielectric constant in the hypodermic area may be changed in response to a change in the concentration of the analyte. At this time, a resonant frequency in a measurement unit 21 of the implant device 20 may be changed in response to a change in the dielectric constant of a surrounding hypodermic area. For example, the measurement unit 21 may include a conducting wire having a specific pattern and a feeder line. In this case, when the dielectric constant of the surrounding hypodermic area is changed, a resonant frequency attributable to the specific pattern and the feeder line may also be changed because capacitance of the measurement unit 21 is changed. An analyte concentration under the skin is changed in proportion to an analyte concentration of a neighbor blood vessel. Accordingly, the biometric information measuring apparatus 10 may finally calculate biometric information, such as an analyte concentration, by using a resonant frequency corresponding to a change in the dielectric constant under the skin.

As an embodiment, the biometric information measuring apparatus 10 may calculate a corresponding relative dielectric constant by using a frequency (e.g., a resonant frequency) at a point at which the size of a scattering parameter is the smallest or greatest.

As an embodiment, the measurement unit 21 of the implant device 20 may be constructed in the form of a resonant device. The implant device 20 may generate a signal by sweeping a frequency within a pre-designated frequency band and inject the generated signal into the resonant device. At this time, the external devices 30 may measure a scattering parameter with respect to the resonant device to which a signal having a varying resonant frequency is supplied.

A communication unit 22 of the implant device 20 may transmit, to the external devices 30, data measured by the measurement unit 21. The communication unit 22 may receive, from the external device 30, power for generating a signal supplied to the measurement unit 21 by using a wireless power transmission method.

The external devices 30 may include a processor 32 and the communication unit 31. The communication unit 31 may receive measurement data (e.g., a scattering parameter or a degree of a change in the resonant frequency) measured by the implant device 20. In this case, the processor 32 of the external devices 30 may determine an analyte concentration based on the measurement data received from the implant device 20. According to an embodiment, the analyte concentration may be directly determined by the external devices 30, but may be determined by the terminal 100 that receives the measurement data from the external devices 30.

As an embodiment, a lookup table (LUT) in which measurement data (e.g., a scattering parameter and/or a degree of a change in the resonant frequency) and analyte concentrations are previously mapped may be stored in the external devices 30. The processor 32 may load an analyte concentration based on the LUT.

Figure 2:
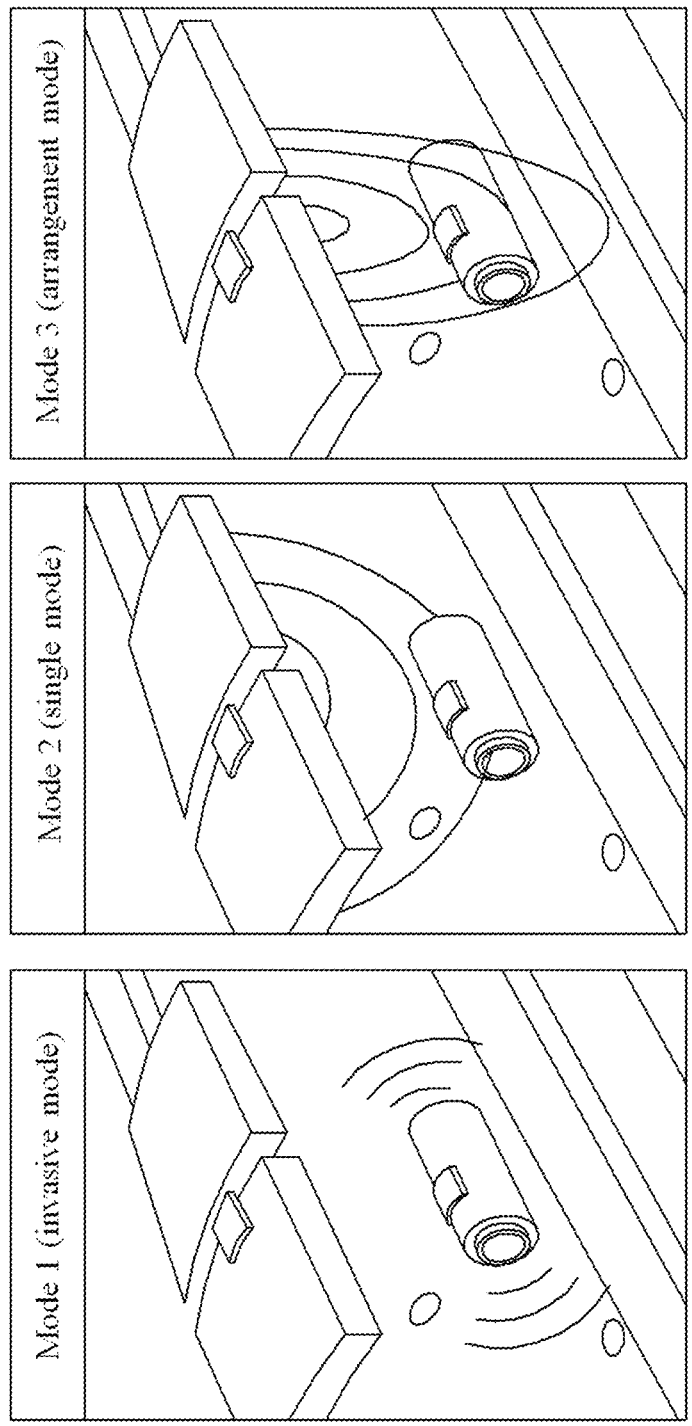
FIG. 2 is an exemplary diagram illustrating three modes of the biometric information measuring apparatus according to an embodiment of the present disclosure.

FIG. 2 is an exemplary diagram illustrating three modes of the biometric information measuring apparatus according to an embodiment of the present disclosure. The biometric information measuring apparatus 10 according to the present embodiment may operate in the three modes. The three modes may be independently performed or may be alternately performed at given time intervals.

<Mode 1: Invasive Mode>

In Mode 1, the biometric information measuring apparatus 10 may directly measure an analyte diffused from a blood vessel of a target to an interstitial fluid within a tissue. For example, an IC chip as the measurement unit 21 of the implant device 20 may radiate an electromagnetic wave having a specific frequency to an analyte, such as glucose around the implant device 20, and may measure a signal reflected and returned from the analyte. Furthermore, the implant device 20 may output a waveform (e.g., a sine wave) of a resonant frequency that varies over time. When a reflection signal according to the frequency in a specific time is detected, the implant device 20 may generate measurement data for biometric information corresponding to the frequency.

<Mode 2: Single Mode>

In Mode 2, at least one external device 30 is provided. Preferably, two external devices 30 may be provided. In this case, in Mode 2, the external devices 30 may include a first external device and a second external device disposed at a given interval.

The biometric information measuring apparatus 10 is coupled to the first external device and the second external device disposed at a given intervals, may measure an electromagnetic wave according to a change in an analyte concentration within an interstitial fluid on the outer surface of the skin of a target analyte, and may calibrate a measured value based on measurement data of biometric information of the implant device 20 along with the measured electromagnetic wave. The biometric information measuring apparatus 10 can improve the accuracy of measurement of an analyte concentration by calibrating a measured value through such a multi-mode.

<Mode 3: Arrangement Mode>

In Mode 1, the implant device 20 of the biometric information measuring apparatus 10 radiates an electromagnetic wave to an analyte around the implant device 20 and measures a signal reflected and returned from the analyte.

In contrast, in Mode 3, the biometric information measuring apparatus 10 radiates an electromagnetic wave that reaches even a depth of a blood vessel of a target analyte, and generates measurement data for biometric information (as an analyte concentration, for example, a blood glucose numerical value) based on a signal reflected and returned from the analyte within the blood vessel.

In general, when an analyte concentration within a blood vessel is changed, the analyte concentration in the hypodermic area may be changed. A dielectric constant in the hypodermic area is changed in response to a change in the analyte concentration.

In Modes 1 and 2, measurement data for biometric information is generated by performing measurement on such a hypodermic area. For this reason, there may be a difference between an analyte concentration within an actual blood vessel and an analyte concentration within a hypodermic area.

Accordingly, the biometric information measuring apparatus 10 can solve a time delay problem with an analyte concentration in a way to obtain measurement data for biometric information within an actual blood vessel by executing an operation, such as Mode 3. Furthermore, a problem which may occur in a target analyte during the time delay can be rapidly checked in advance because a sudden change in the analyte concentration of the target analyte can be measured by Mode 3.

Furthermore, the biometric information measuring apparatus 10 according to an embodiment can measure biometric information more accurately in a way to calibrate a value of an analyte concentration by simultaneously operating two or more of the three modes. For example, the biometric information measuring apparatus 10 according to the present embodiment can secure accuracy in a way to secure the diversity of data by simultaneously using Modes 1 and 2 of the implant device 20, and can improve the accuracy of measurement of biometric information through a repetition test.

Furthermore, the biometric information measuring apparatus 10 according to an embodiment can solve the time delay problem, that is, a problem with conventional interstitial fluid sensors for measuring biometric information, by improving a penetration depth of an electromagnetic wave radiated using Mode 3 and monitoring a change in the analyte concentration within a blood vessel in real time.

Furthermore, as described above, the diversity of data can be secured by using a plurality of sensors and a plurality of modes together. The accuracy of a method of predicting biometric information can be improved and a reappearance issue can be solved by adjusting a calibration cycle.

As an embodiment, the biometric information measuring apparatus 10 may predict an analyte concentration by associating, with a Bayesian filter-based algorithm, measurement data of another sensor (e.g., an environment sensor, a temperature sensor or a humidity sensor) along with measurement data measured by Modes 1, 2, and 3.

Furthermore, the biometric information measuring apparatus 10 according to an embodiment may simultaneously use Modes 1 and 2 in order to secure the reappearance of measurement of a dielectric constant, and may perform re-measurement when analyte concentrations measured based on measurement data of Mode 1 and measurement data of Mode 2 are not the same, or may measure an analyte concentration through blood-gathering, may input the measured analyte concentration, and may perform calibration.

As described above, the biometric information measuring apparatus 10 may perform mutual verification on the results of measurement when values of analyte concentrations measured in multiple modes are the same based on a plurality of measurement data obtained in the multiple modes, and may request to measure an analyte concentration of a target analyte through blood-gathering only when values of analyte concentrations measured in the multiples modes are different in order to reduce the number of times of blood-gathering for the target analyte.

Figure 3:
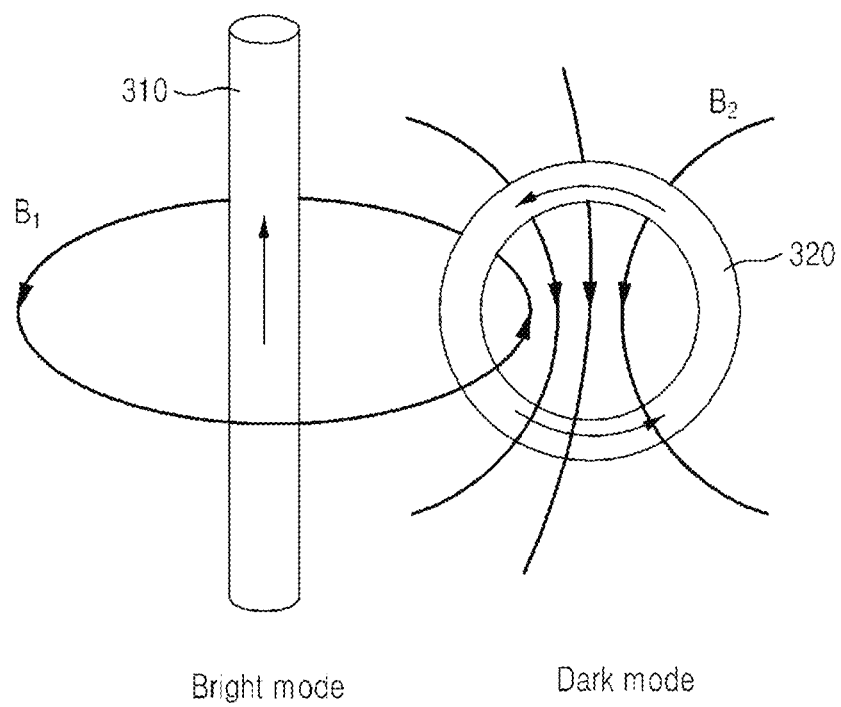
FIG. 3 is a diagram for describing a dark mode according to an embodiment of the present disclosure.

FIG. 3 is a diagram for describing a dark mode according to an embodiment of the present disclosure. When a bright mod having a duplication behavior interacts with a sub-radiated dark mode, resonance of a trapped mode may occur. Such a trapped mode may have a very high Q coefficient because the resonance is characterized by a strong local field. In an electromagnetic area, short-range coupling may be used to excite the trapped mode. FIG. 3 illustrates an example in which a field $B_1$ in the bright mode, which is generated by the electric dipole of a dipole antenna 310, is combined with a loop 320 to generate a current circulating in the loop 320 and a magnetic field $B_2$ is generated in the dark mode through the generated current. For example, when the dipole antenna 310 is disposed in the external devices 30 and the loop 320 is disposed in the implant device 20, the loop 320 of the implant device 20 may process the sensing of an analyte through a current induced from the dipole antenna 310 of the external devices 30 even without separate power supply.

Figure 4:
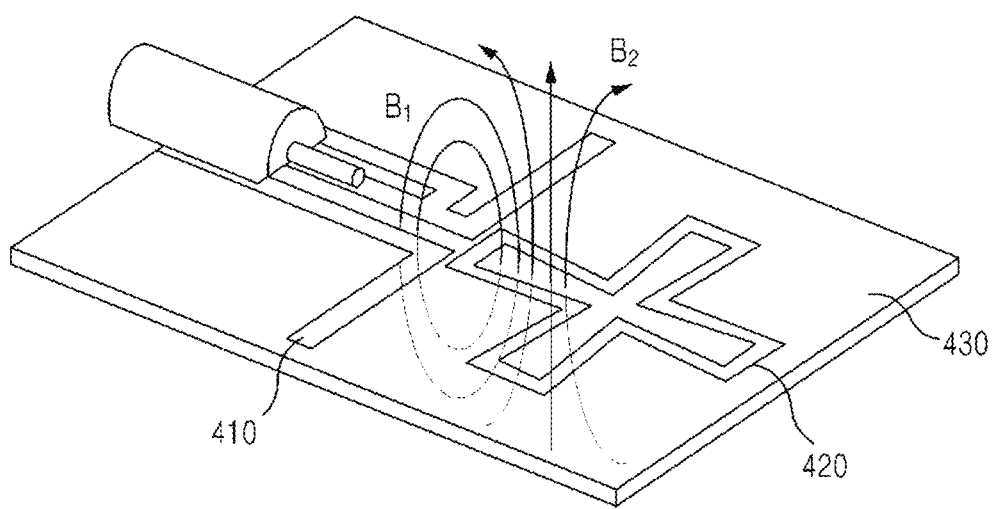
FIG. 4 is a diagram illustrating an example of a sensor having electric quadrupole moment according to an embodiment of the present disclosure.

FIG. 4 is a diagram illustrating an example of a sensor having electric quadrupole moment according to an embodiment of the present disclosure. As in FIG. 3, a magnetic field $B_1$ generated by the electric dipole of a dipole antenna 410 may induce a current through an interaction with a loop 420. A total length of the loop may be a length that is half of a wavelength λ corresponding to the frequency of a supplied feeding signal. A current distribution in the loop 420 shows the presence of electric quadrupole moment due to the total length of the loop and a current distribution, and may cause sharp peak resonance in the middle of wide dipole resonance. The embodiment of FIG. 4 illustrates an example in which both the dipole antenna 410 and the loop 420 are formed in one board 430. However, as already described, the dipole antenna 410 may be disposed in the external devices 30 disposed on the exterior of a target analyte, and the loop 420 may be disposed in the implant device 20 inserted into the body. In this case, the loop 420 of the implant device 20 can process the sensing of the analyte through a current induced from the dipole antenna 410 of the external devices 30 to the loop 420 and a corresponding magnetic field $B_2$ even without separate power supply. The conducting wire forms the loop 420 so that a cross-shaped is included.

Figure 5:
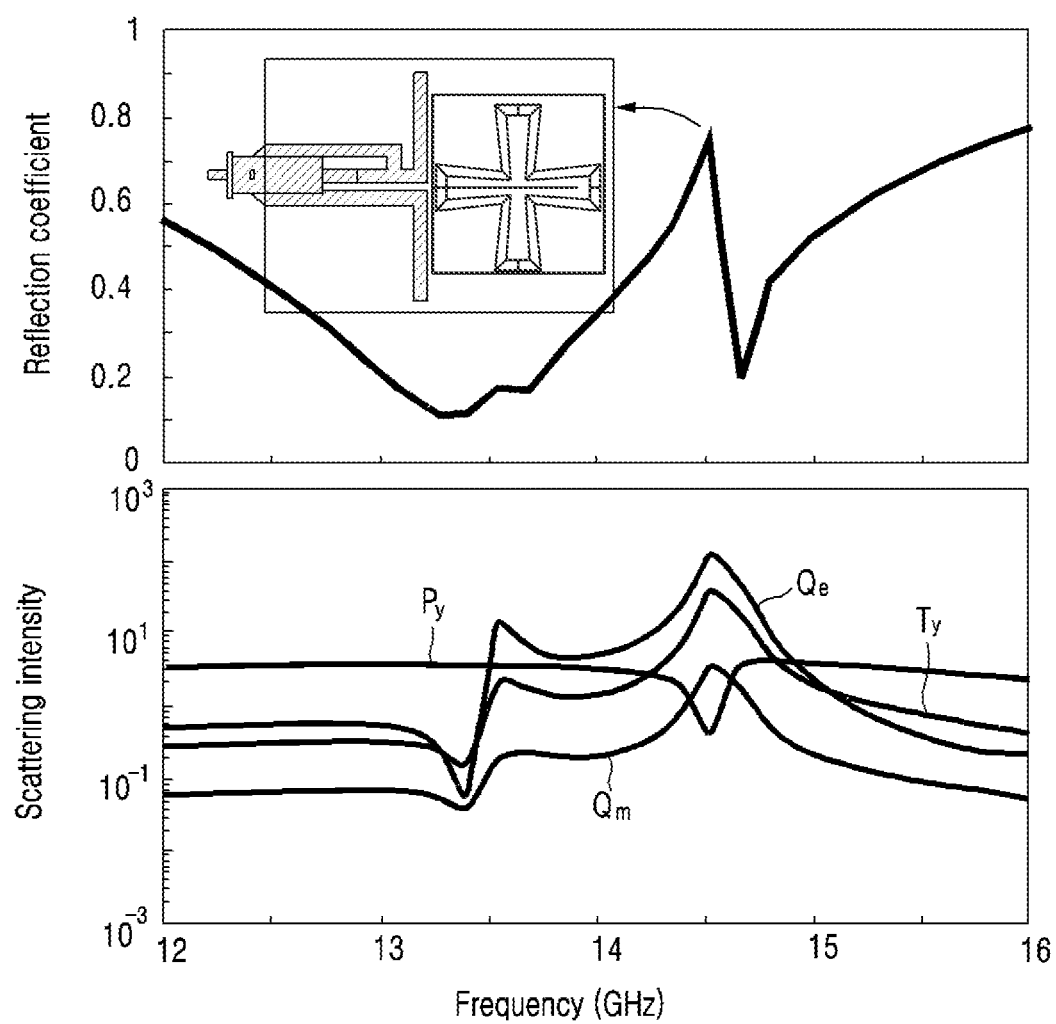
FIG. 5 illustrates graphs showing examples of electric quadrupole moment according to an embodiment of the present disclosure.

FIG. 5 illustrates graphs showing examples of electric quadrupole moment according to an embodiment of the present disclosure. FIG. 5 illustrates reflection coefficients and scattering intensity according to frequencies. The graphs of FIG. 5 illustrate that sharp peak resonance is caused in the middle of dipole resonance attributable to the dipole antenna 410 due to the loop 420 having electric quadrupole moment. In this case, P and T may mean moment of an electric dipole and moment of a toroidal dipole, respectively. Since the moment has a vector quantity, x, y, and z may mean three-dimensional vector components. $Q_e$ may mean an electric quadrupole, and $Q_m$ may mean a magnetic quadrupole.

Figure 6:
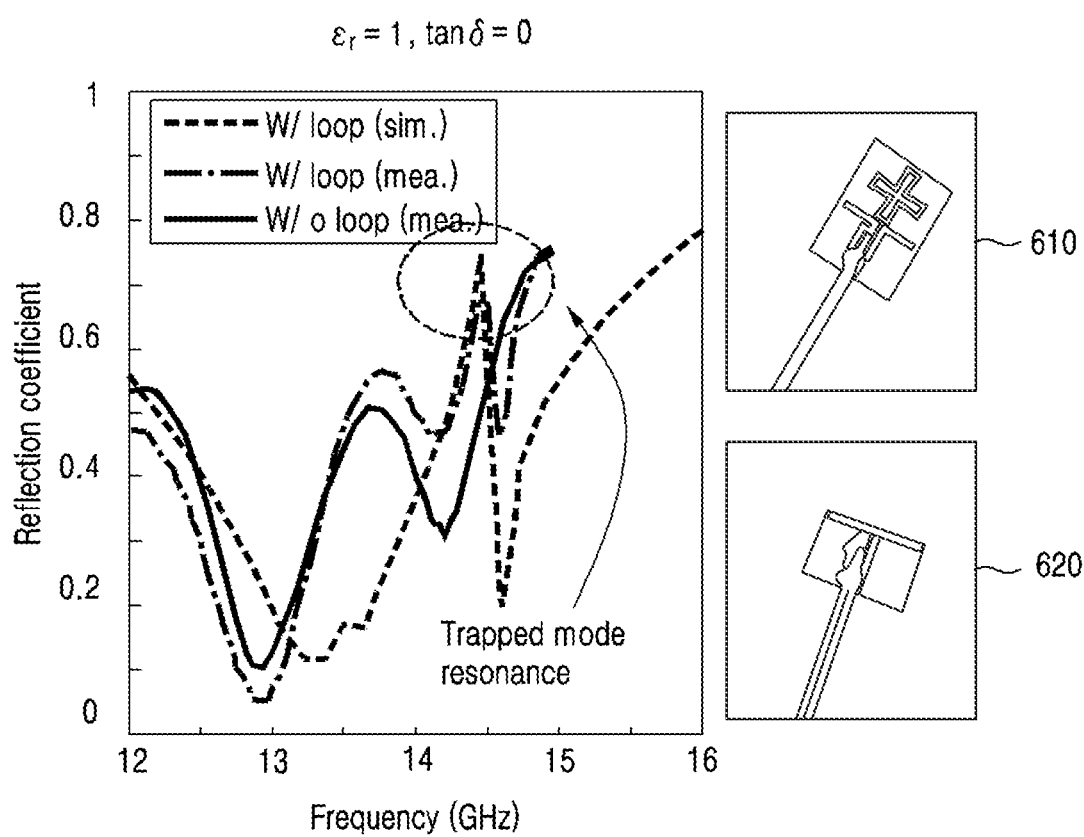
FIGS. 6 to 8 are graphs illustrating examples of simulations and measuring results for the sensor having electric quadrupole moment according to an embodiment of the present disclosure.
Figure 7:
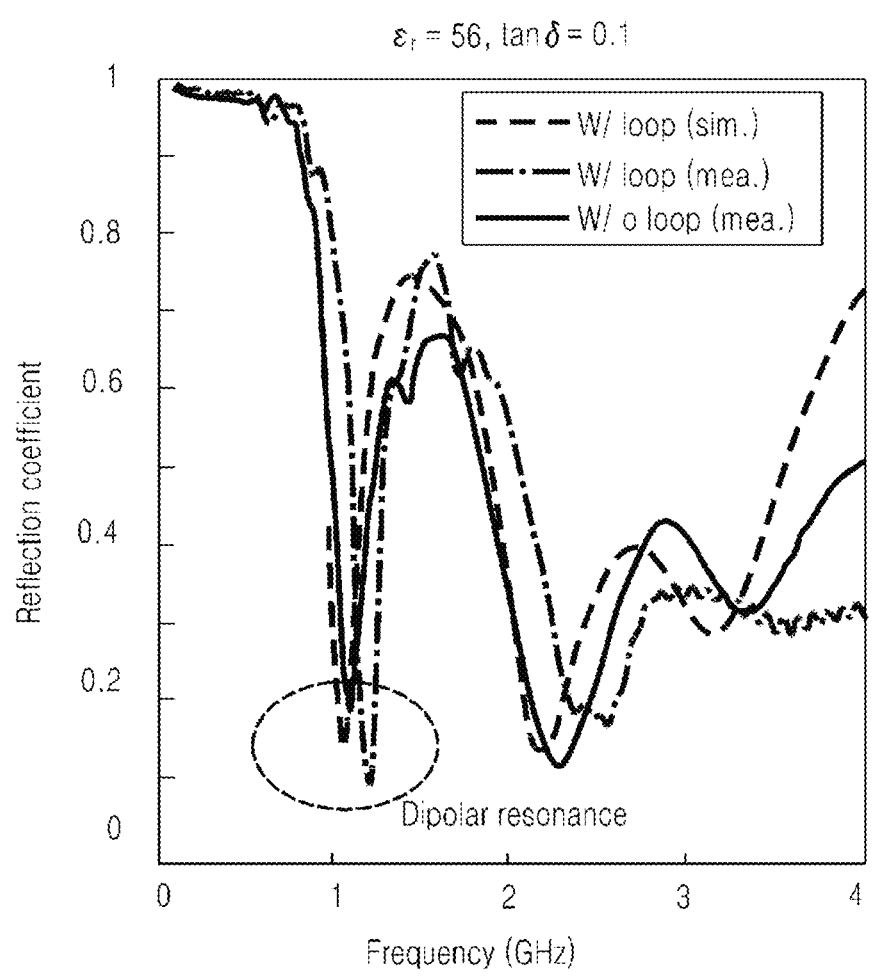
Figure 8:
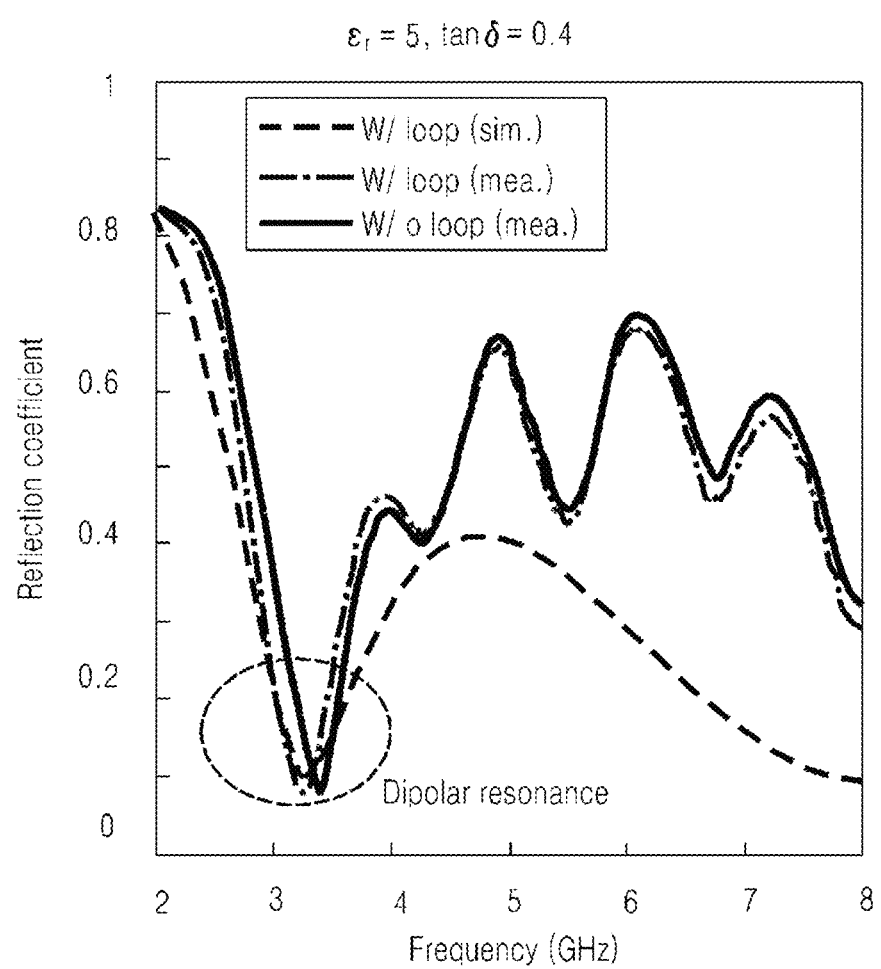

FIGS. 6 to 8 are graphs illustrating examples of simulations and measuring results for the sensor having electric quadrupole moment according to an embodiment of the present disclosure. FIG. 6 illustrates simulations and measuring results in the air. FIG. 7 illustrates simulations and measuring results in the water at room temperature. FIG. 8 illustrates simulations and measuring results when the loop was added within pork fat and a current was induced from the outside of the pork fat to the dipole antenna. In the graphs, "W/" may mean "with", and "W/O" may mean "without." A first photo 610 in FIG. 6 illustrates an example when both the dipole antenna and the loop were present (W/loop). A second photo 620 in FIG. 6 illustrates an example when only the dipole antenna is present without the loop (W/O loop). From the graphs of FIGS. 6 to 8, it may be seen that the simulations and the measuring results are well matched. However, measured data shows that a trapped mode disappears in a lost material, that is, water and fat, and dipole resonance remains.

Figure 9:
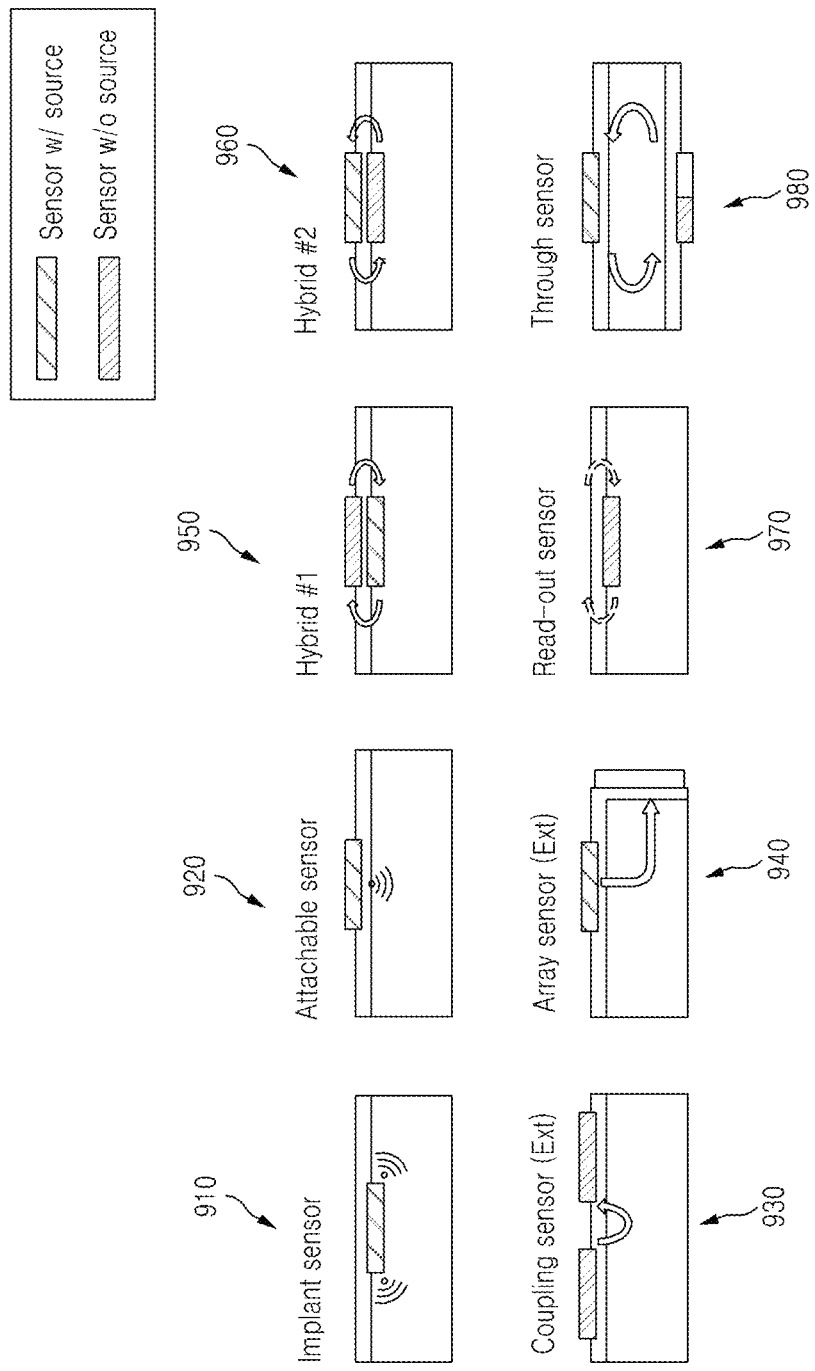
FIG. 9 illustrates diagrams showing examples of various measurement modes according to an embodiment of the present disclosure.

FIG. 9 illustrates diagrams showing examples of various measurement modes according to an embodiment of the present disclosure.

A first mode 910 illustrates an example of a mode in which the implant device 20 having a power source directly senses information on an analyte within the body having a target analyte through an implant sensor. The first mode 910 may correspond to the invasive mode described with reference to FIG. 2.

A second mode 920 illustrates an example of a mode in which the external devices 30 having a power source senses information on an analyte within the body having a target analyte in the state in which the external devices 30 has been disposed on the exterior of the target analyte.

A third mode 930 and a fourth mode 940 illustrate examples of modes in which information on an analyte within the body having a target analyte is sensed through coupling between a plurality of external devices attached to the exterior of the target analyte. The third mode 930 and the fourth mode 940 may correspond to the single mode and the arrangement mode described with reference to FIG. 2, respectively. In this case, the third mode may be a powerless sensing method of processing sensing through a current induced using the trapped mode according to the sensor of the implant device 20 having a power source inserted into the body without a separate power source.

A fifth mode 950 and a sixth mode 960 correspond to a hybrid mode, and illustrate an example of a mode in which information on an analyte within the body having a target analyte is sensed through coupling between an in-vitro sensor of the external devices 30 disposed on the exterior of the target analyte and an implant sensor of the implant device 20 inserted into the body having the target analyte. For example, a side having a power source may include a dipole antenna, and a side not having a power source may include a sensor loop. In this case, a strong magnetic field may be formed in the sensor loop through a magnetic field radiated by the dipole antenna. Information on the target analyte within the body may be sensed using the strong magnetic field formed in the sensor loop.

A seventh mode 970 illustrates an example of a mode in which the implant device 20 not having a power source includes a sensor loop and information on an analyte within the body having a target analyte is sensed by temporarily inducing a current and a magnetic field into the sensor loop through the approach of a dipole antenna including a separate reader.

An eighth mode 980 illustrates an example of a mode in which the external devices 30 are disposed on both sides of a relatively thin body portion like an earlobe, respectively, and sense information on an analyte within the body having a target analyte.

Figure 10:
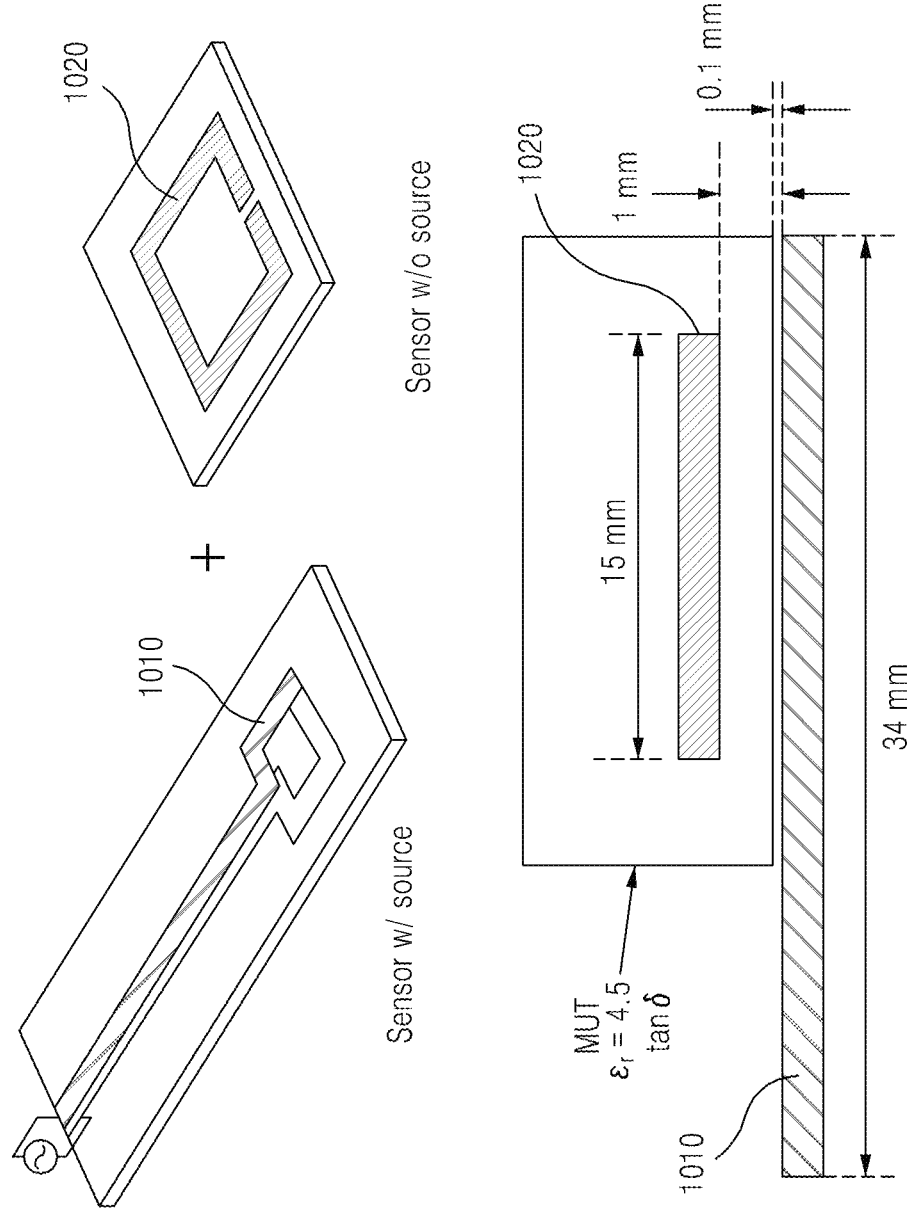
FIG. 10 is a diagram for describing an example of a hybrid mode in an embodiment of the present disclosure.

FIG. 10 is a diagram for describing an example of a hybrid mode in an embodiment of the present disclosure. The embodiment of FIG. 10 illustrates an example of the hybrid mode using a first sensor 1010 having a power source and a second sensor 1020 not having a power source. In this case, a current and a magnetic field may be induced into the second sensor 1020 due to a magnetic field radiated by power supplied to the first sensor 1010. The second sensor 1020 may sense information on an analyte based on the induced magnetic field.

Figure 11:
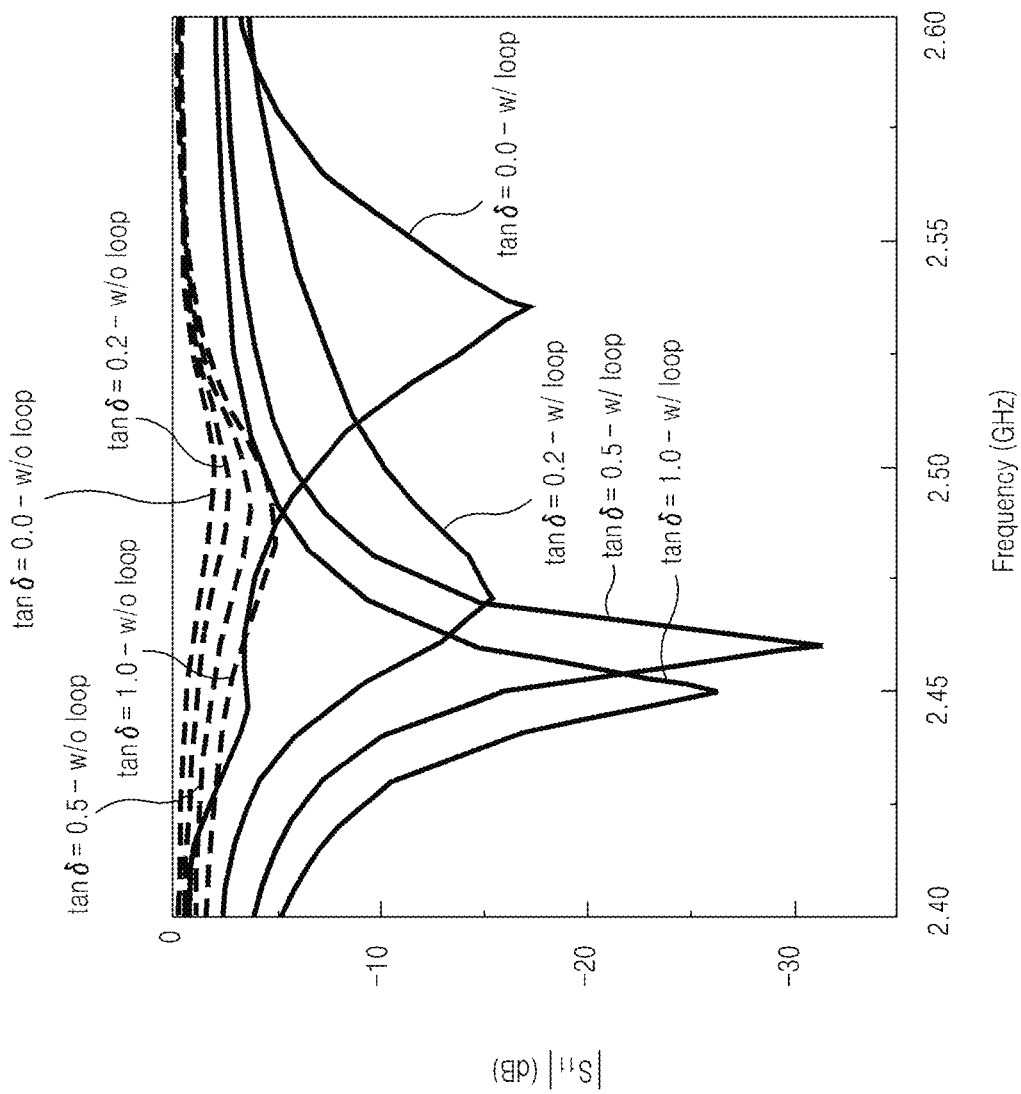
FIG. 11 is a graph illustrating scattering parameters $S_{11}$ according to whether a loop is present, a lost material and a frequency in an embodiment of the present disclosure.

FIG. 11 is a graph illustrating scattering parameters $S_{11}$ according to whether a loop is present, a lost material and a frequency in an embodiment of the present disclosure. In this case, the scattering parameter $S_{11}$ may be information on a measured value measured in a first antenna when a magnetic field radiated by the first antenna of a two-port antenna returns to the first antenna again due to reflection. A scattering parameter $S_{21}$ may be information on a measured value measured in a second antenna with respect to the magnetic field radiated by the first antenna.

Figure 12:
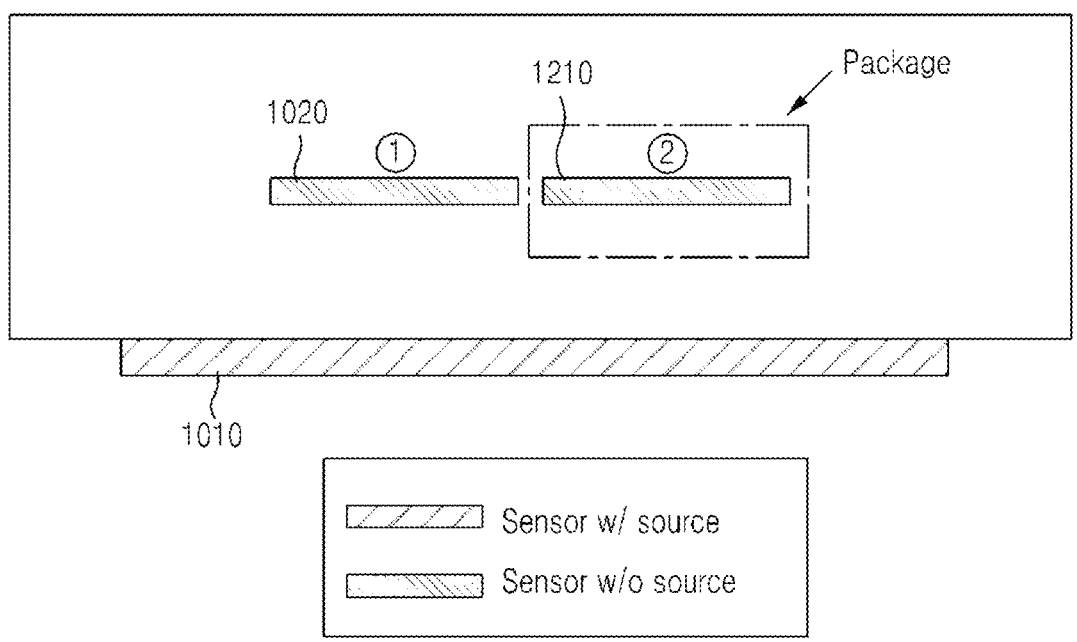
FIG. 12 is a diagram for describing another example of the hybrid mode in an embodiment of the present disclosure.

FIG. 12 is a diagram for describing another example of the hybrid mode in an embodiment of the present disclosure. The embodiment of FIG. 12 illustrates an example of the hybrid mode using a third sensor 1210 surrounded by a package without a power source, in addition to a first sensor 1010 having a power source and a second sensor 1020 not having a power source. In this case, the second sensor 1020 may be sensitive to an analyte level, and the third sensor 1210 surrounded by the package may have a relatively less sensitive analyte level than the second sensor 1020. According to an embodiment, the package may be filled with a special material. The third sensor is relatively sensitive to a temperature or a movement of a target analyte, and thus can remove an environment influence because the third sensor operates as a reference sensor for correction purposes. According to an embodiment, the second sensor 1020 and the third sensor 1210 may be implemented to have pieces of different polarization in order to distinguish between responses.

Figure 13:
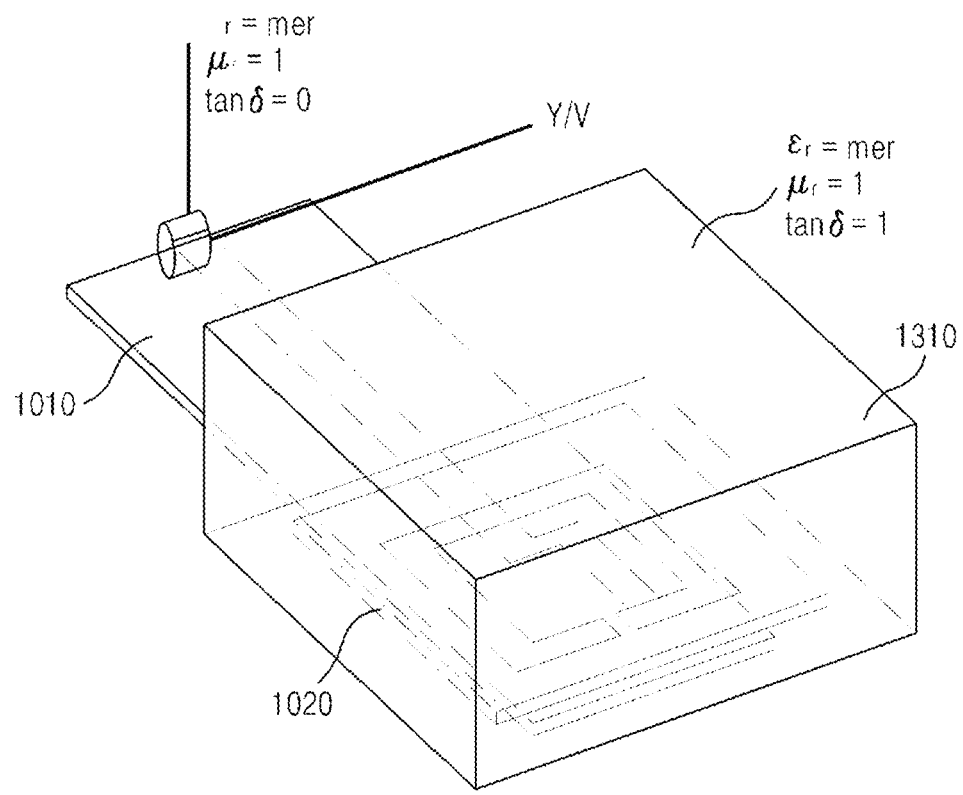
FIGS. 13 to 16 are experiment examples for measuring a frequency response in the hybrid mode according to an embodiment of the present disclosure.
Figure 14:
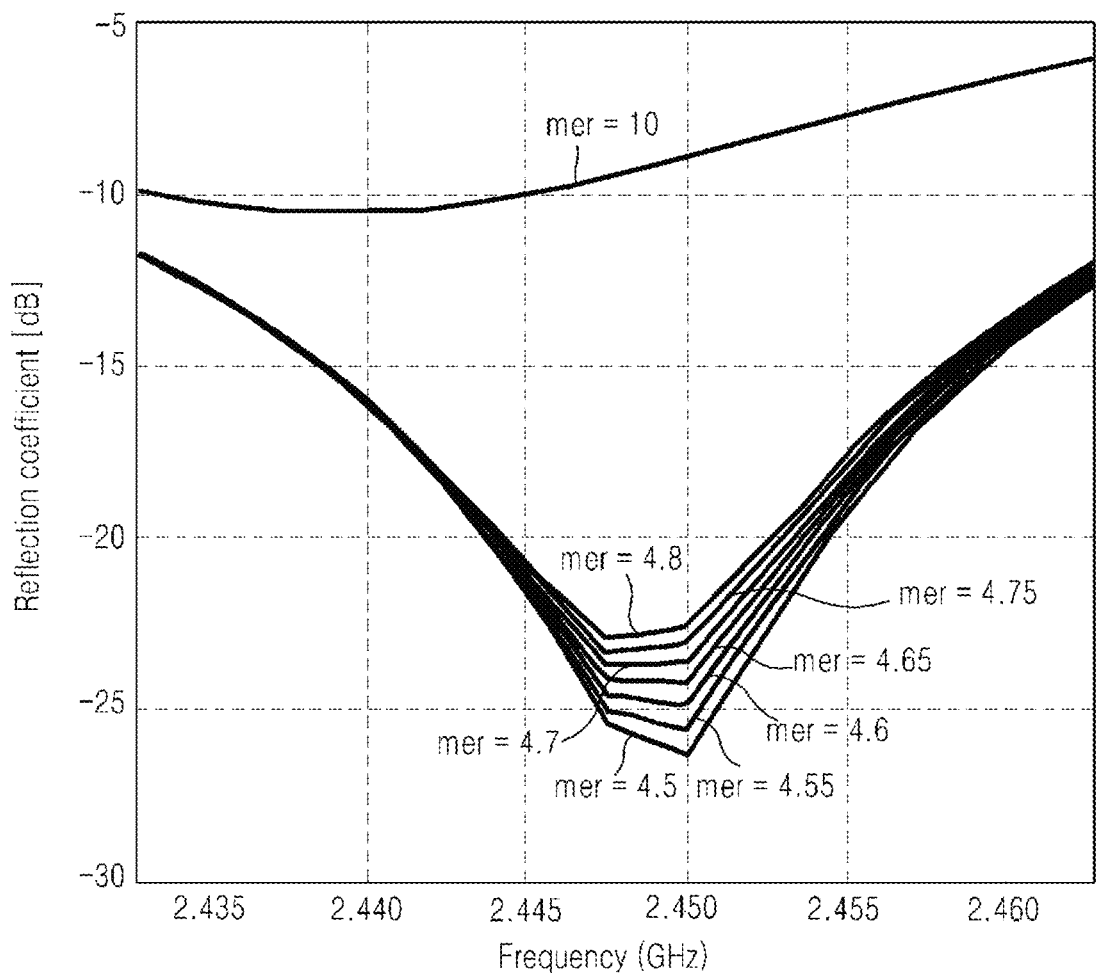
Figure 15:
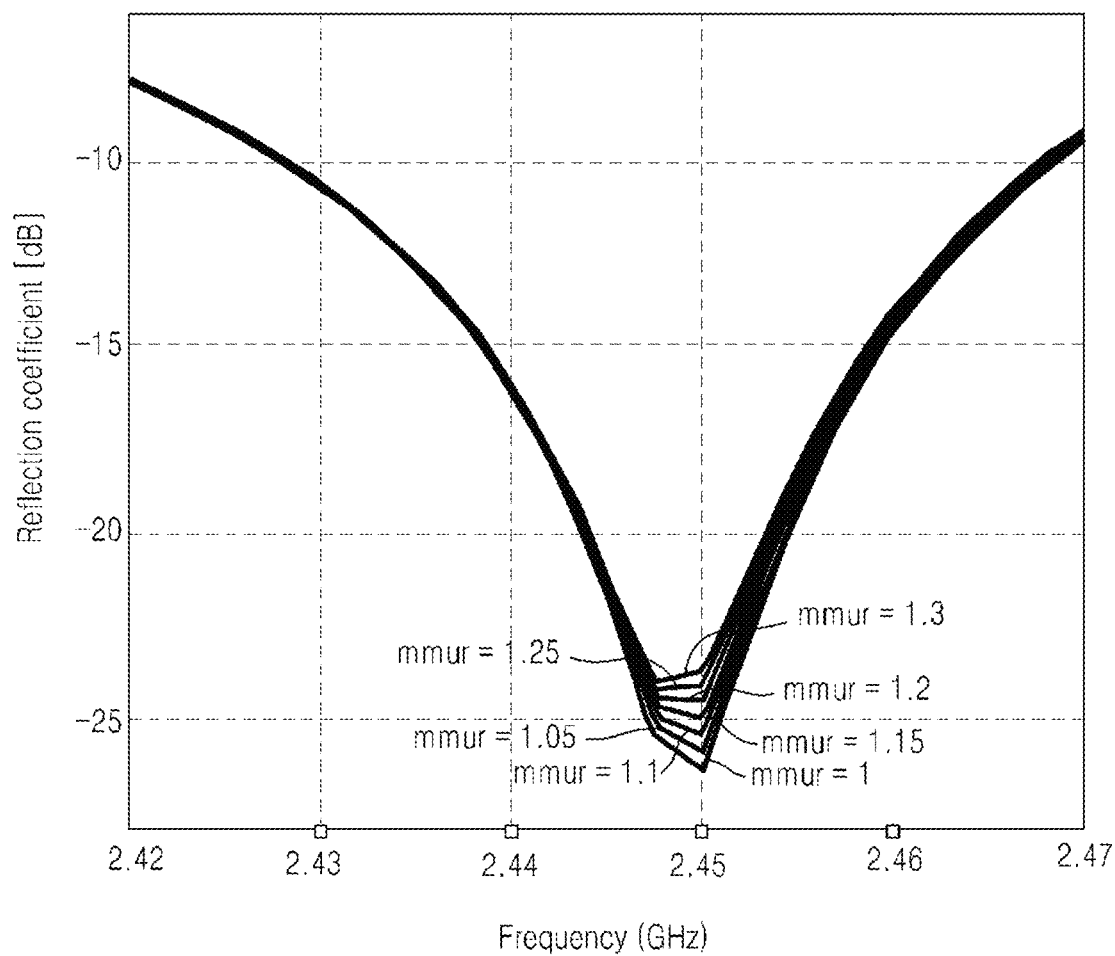
Figure 16:
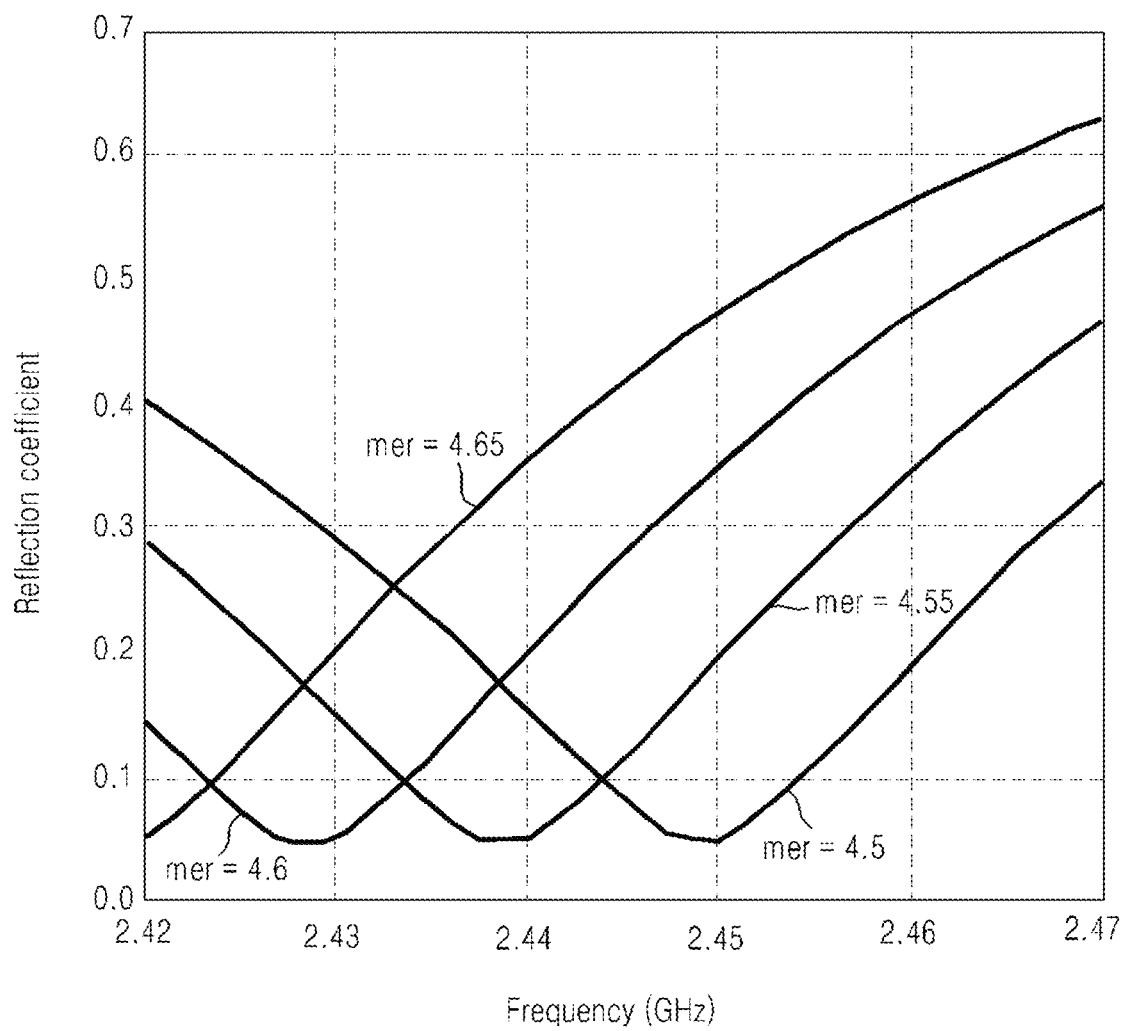

FIGS. 13 to 16 are experiment examples for measuring a frequency response in the hybrid mode according to an embodiment of the present disclosure. FIG. 13 illustrates an example of the hybrid mode using the first sensor 1010 having a power source and the second sensor 1020 not having a power source. In this case, in the embodiment of FIG. 13, the experiment was performed by disposing the second sensor 1020 within a material 1310 for implementing various dielectric constants in a given loss (tan δ=1). In this case, graphs of FIGS. 14 and 15 illustrate that a change in the dielectric constant is incorporated into reflection coefficients. A graph of FIG. 16 illustrates that a shift in the frequency may occur depending on the setting of the sensors 1010 and 1020.

Figure 17:
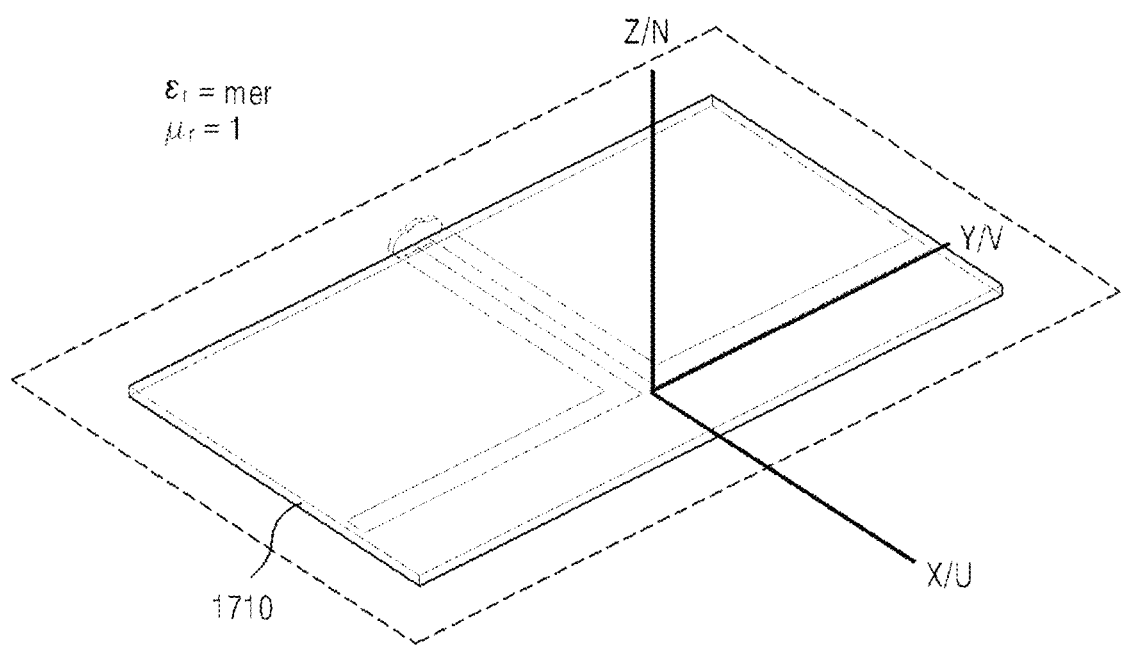
FIG. 17 is a diagram illustrating an example of a dipole antenna in an embodiment of the present disclosure.
Figure 18:
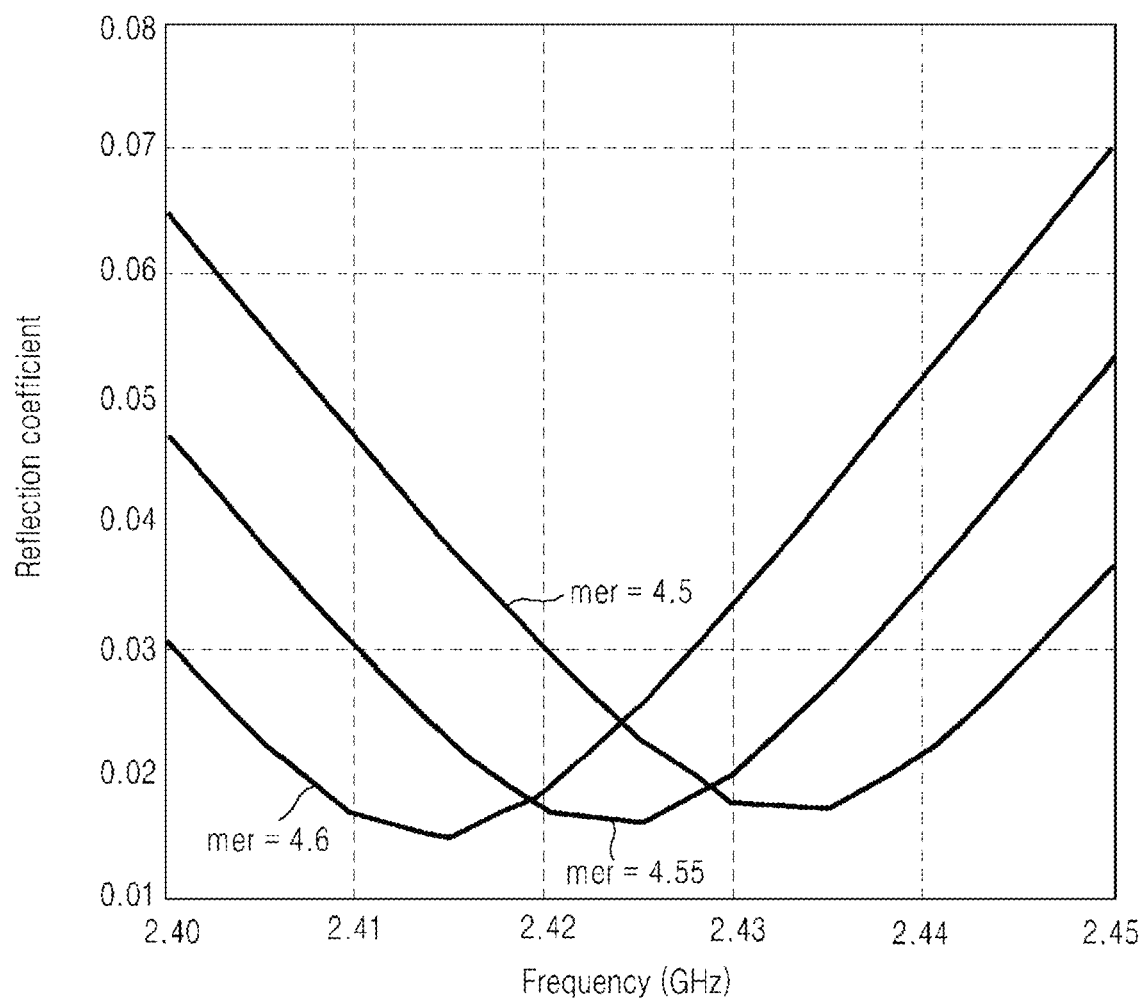
FIG. 18 is a graph illustrating the measurement of frequency response characteristics when the dipole antenna is used in an embodiment of the present disclosure.

FIG. 17 is a diagram illustrating an example in which a dipole antenna is used in an embodiment of the present disclosure. FIG. 18 is a graph illustrating the measurement of frequency response characteristics when the dipole antenna is used in an embodiment of the present disclosure. The embodiment of FIG. 17 illustrates that the hybrid mode can be implemented using a dipole antenna 1710 instead of the first sensor 1010. In this case, it may be seen that when the dipole antenna 1710 is used, sensitivity becomes higher compared to the graphs of FIGS. 18 and 16.

Figure 19:
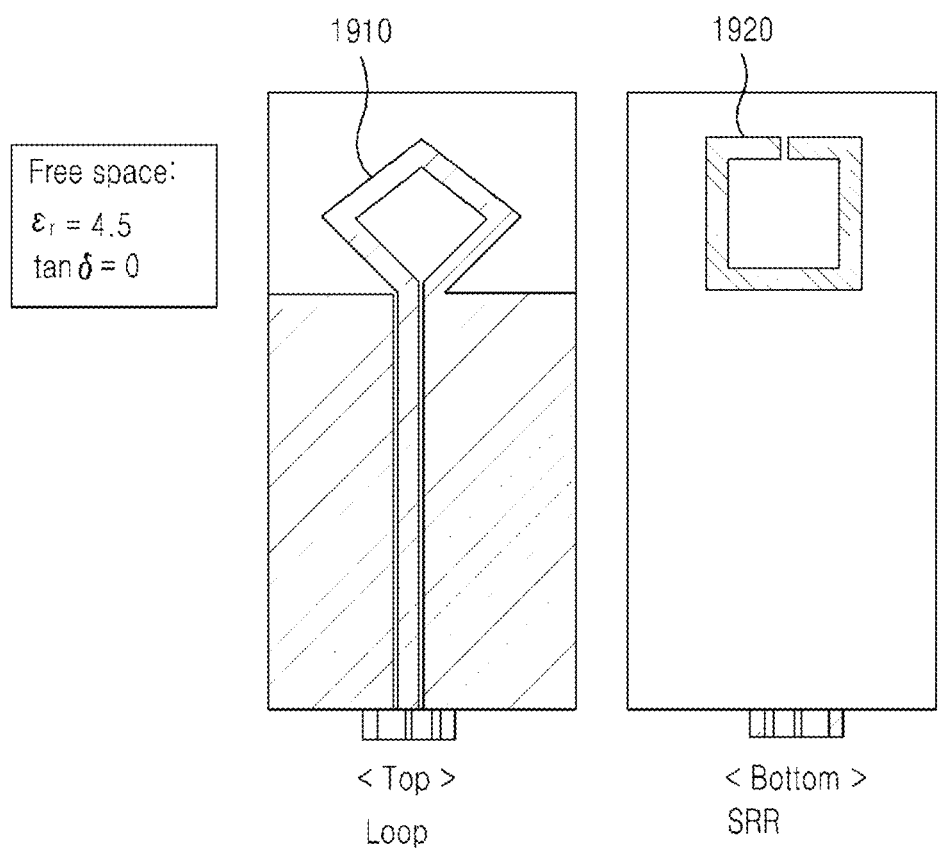
FIGS. 19 to 21 are diagrams for describing other examples of the hybrid mode in an embodiment of the present disclosure.
Figure 20:
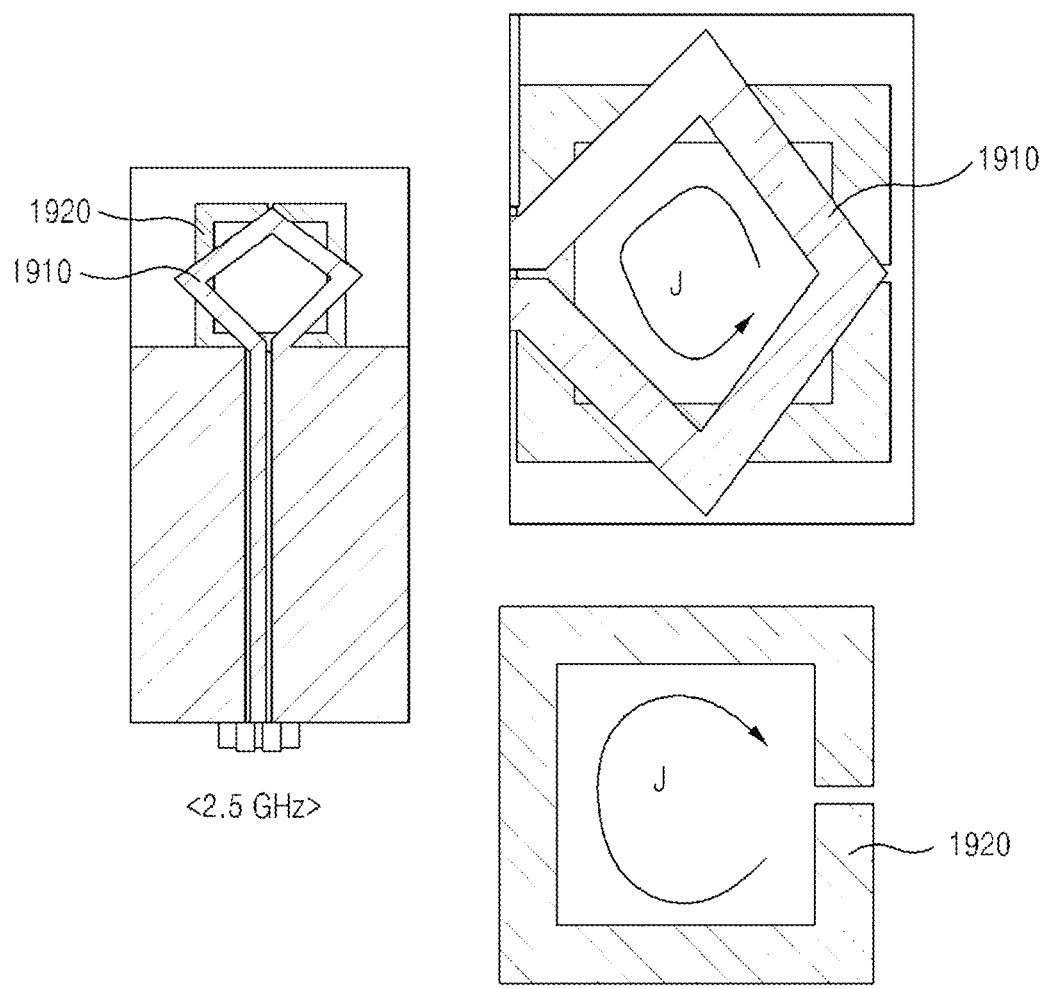
Figure 21:
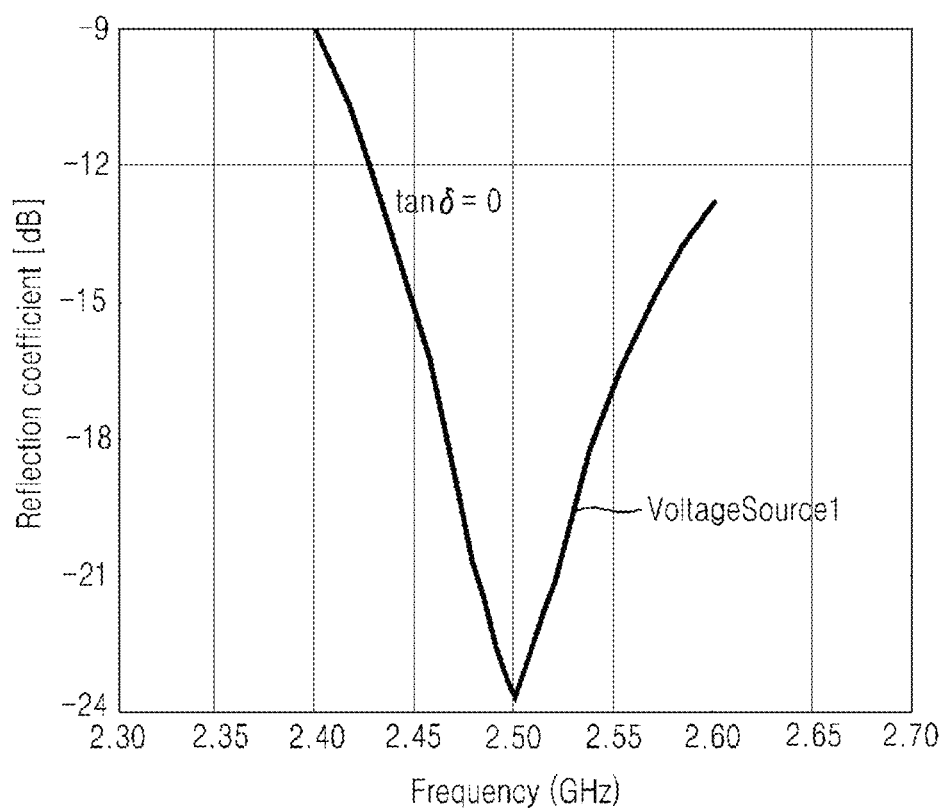

FIGS. 19 to 21 are diagrams for describing other examples of the hybrid mode in an embodiment of the present disclosure. FIGS. 19 and 20 illustrate examples of a first sensor 1910 having a power source and a second sensor 1920 having a power source. In this case, the first sensor 1910 was intended to reduce the complexity of fabrication by using coplanar waveguide (CPW) feeding instead of a design in which a power source is supplied by a microstrip line. FIGS. 19 to 21 illustrate examples for increasing sensitivity so that a current is induced to the opposite side by using a dummy loop to which a power source is connected as the second sensor 1920. According to an embodiment, the second sensor 1920 may be replaced with the loop 420 described with reference to FIG. 4. A graph of FIG. 21 illustrates frequency response characteristics when the first sensor 1910 and the second sensor 1920 illustrated in FIGS. 19 and 20 according to an embodiment were used, and illustrates that peak resonance is well formed.

Figure 22:
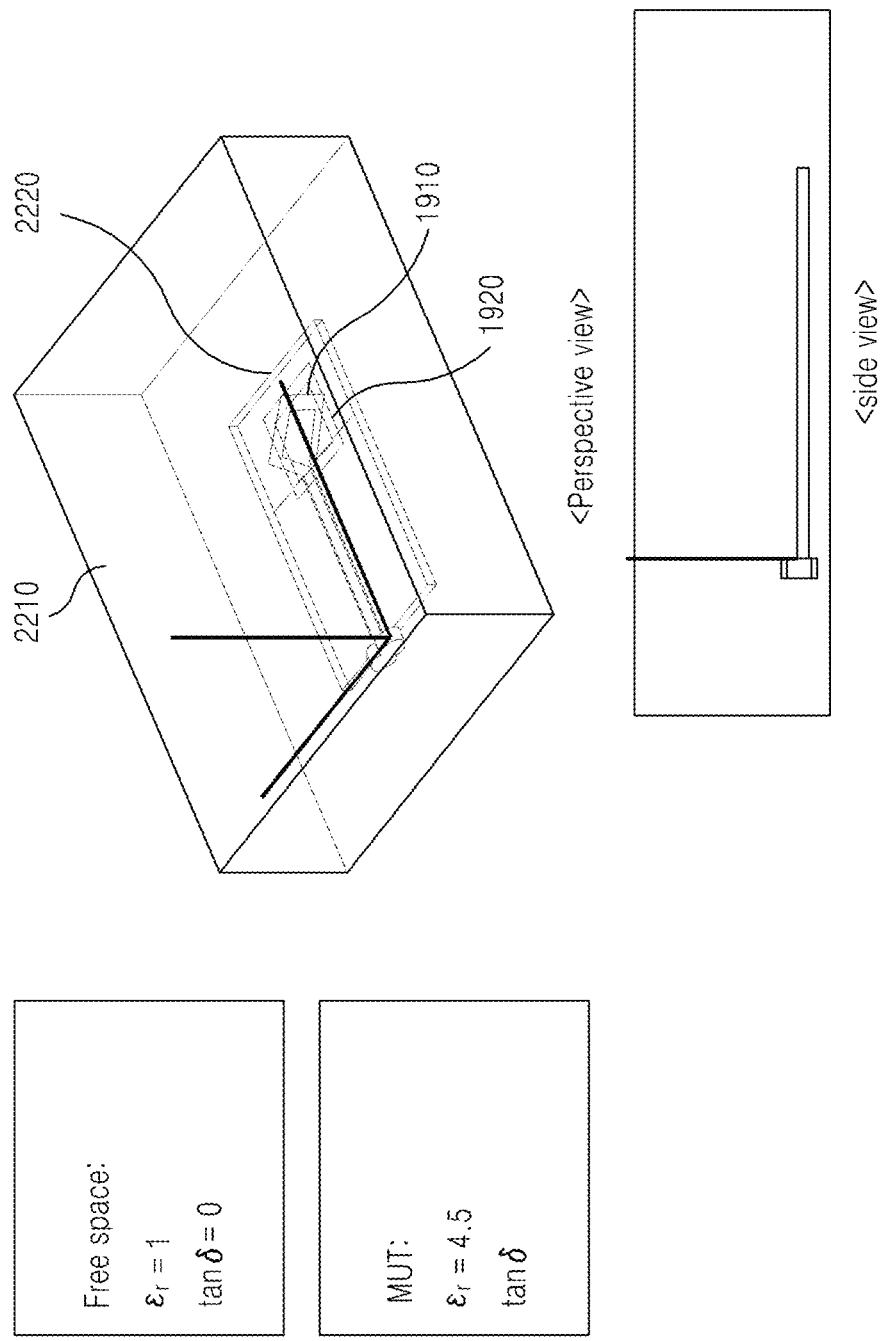
FIGS. 22 to 24 are diagrams illustrating a first example of frequency response experiments according to an embodiment of the present disclosure.
Figure 23:
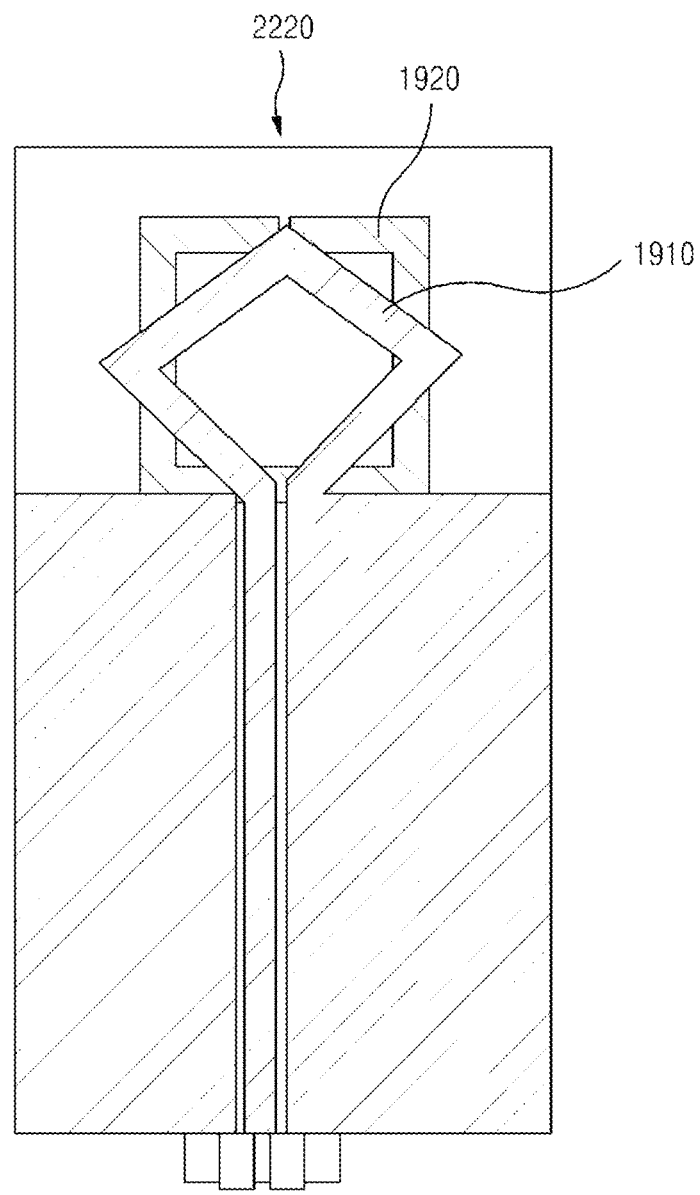
Figure 24:
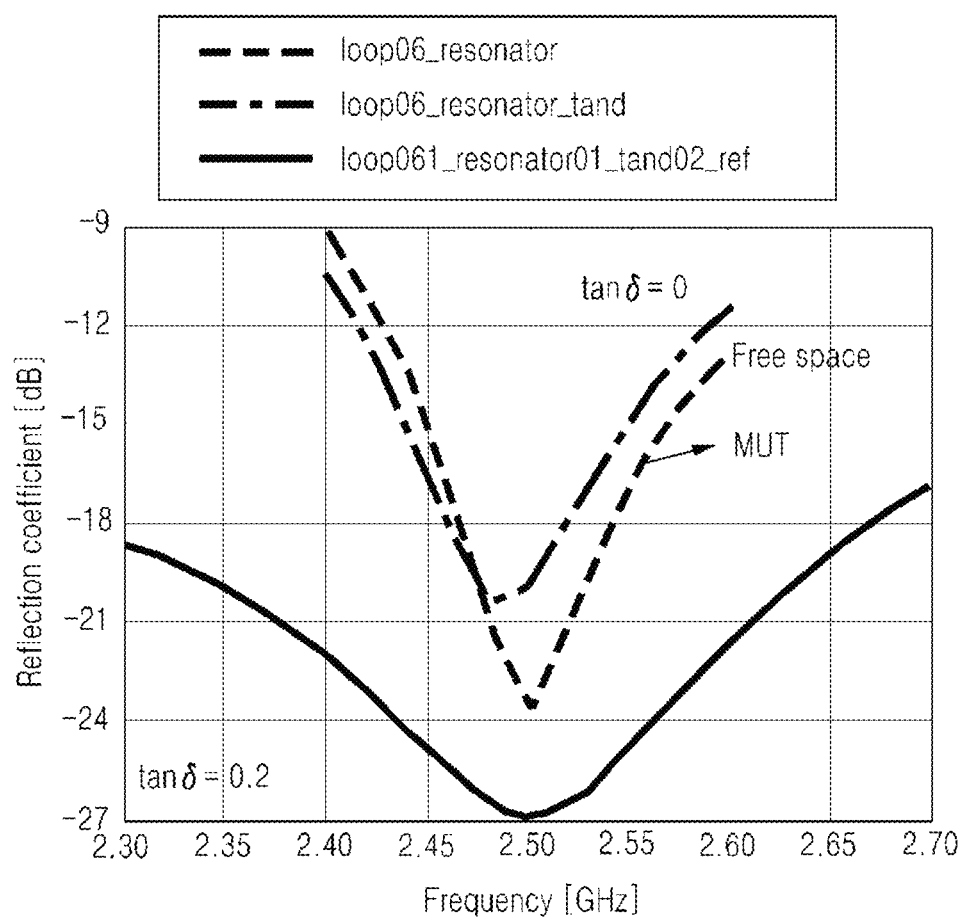

FIGS. 22 to 24 are diagrams illustrating a first example of frequency response experiments according to an embodiment of the present disclosure. In this case, FIG. 22 illustrates an example in which a sensor 2220 having the first sensor 1910 and the second sensor 1920 combined therewith was disposed within a material under test (MUT) 2210, that is, a material having a specific dielectric constant, and experiments were performed on frequency response characteristics. In this case, as illustrated in FIG. 23, the sensor 2220 may be implemented so that the first sensor 1910 is disposed over the second sensor 1920. A graph of FIG. 24 illustrates an example of the results of the frequency response characteristics using the sensor 2220 illustrated in FIGS. 22 and 23. The graph of FIG. 24 illustrates that peak resonance is well formed in both a free space and the MUT 2210.

Figure 25:
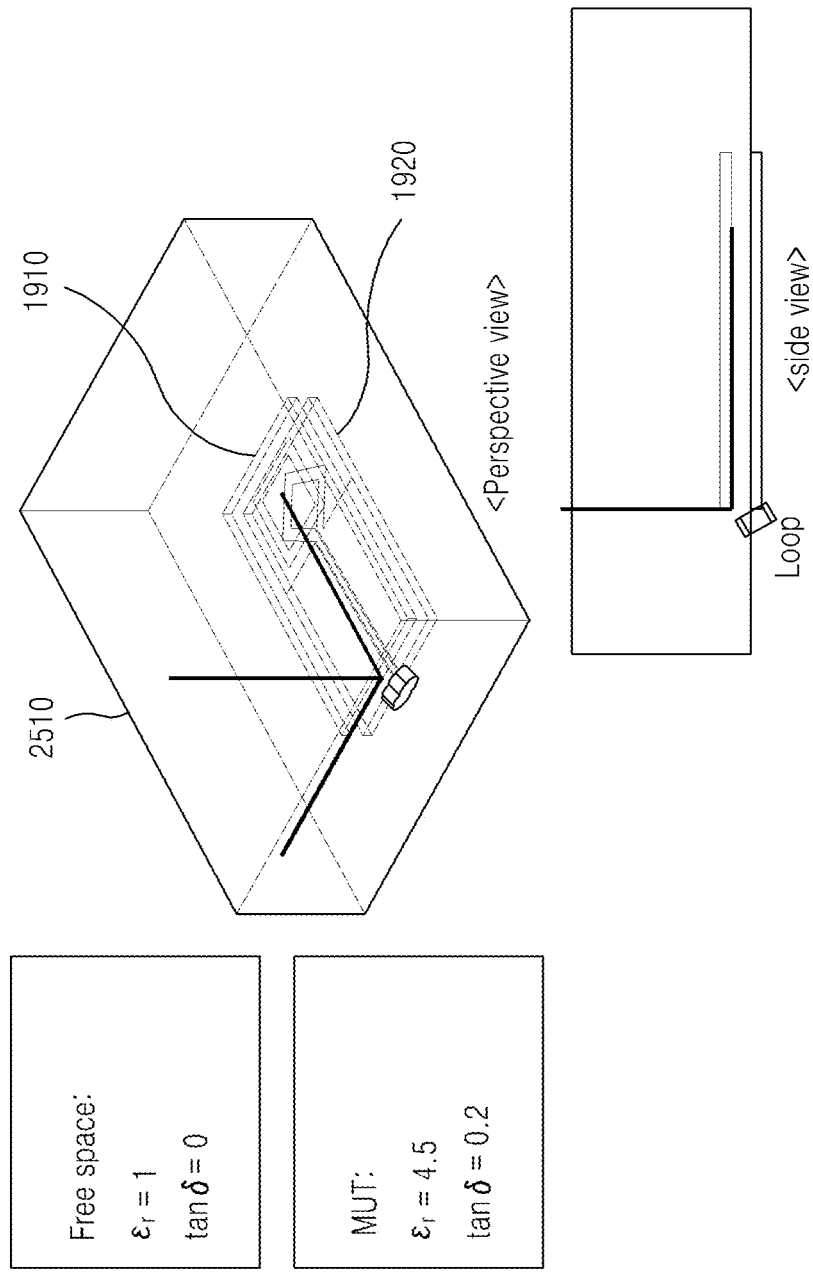
FIGS. 25 to 27 are diagrams illustrating a second example of frequency response experiments according to an embodiment of the present disclosure.
Figure 26:
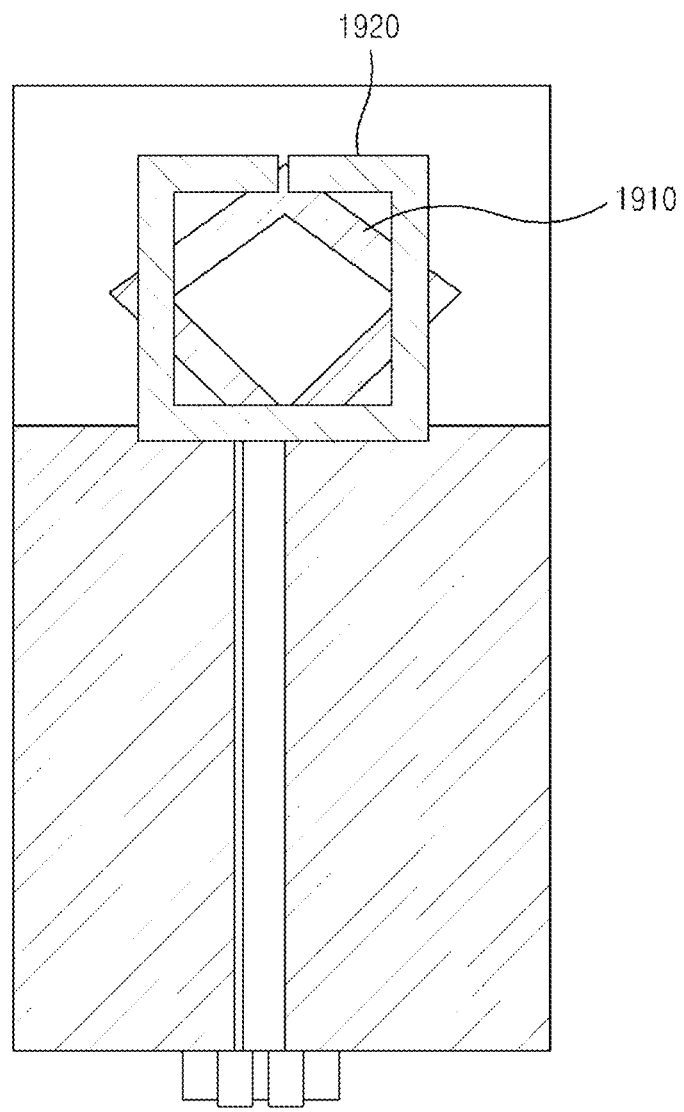
Figure 27:
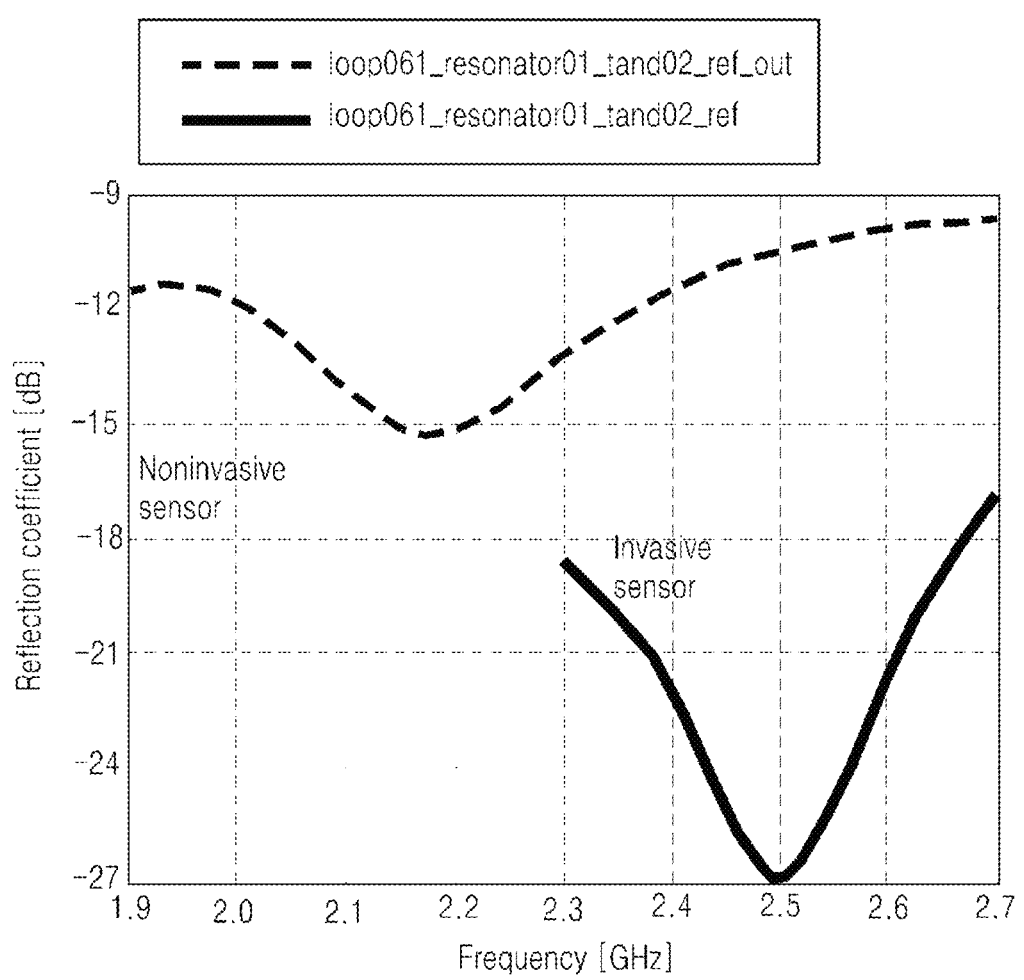

FIGS. 25 to 27 are diagrams illustrating a second example of frequency response experiments according to an embodiment of the present disclosure. FIG. 25 illustrates an example in which the second sensor 1920 was disposed within a MUT 2510, that is, a material having a specific dielectric constant, the first sensor 1910 was disposed outside the MUT 2510, and experiments were performed on frequency response characteristics. In this case, as illustrated in FIG. 26, the second sensor 1920 may be disposed over the first sensor 1910 within the MUT 2510. From a graph of FIG. 27, it may be seen that if the first sensor 1910, that is, a loop including a power source, is disposed outside the MUT 2510, resonance is still monitored although the resonance is not clear as much as an invasive sensor. Such a reduction of sensitivity may occur due to a loss "link" between the first sensor 1910 and the second sensor 1920, that is, a loop, and an error of a numerical value.

Figure 28:
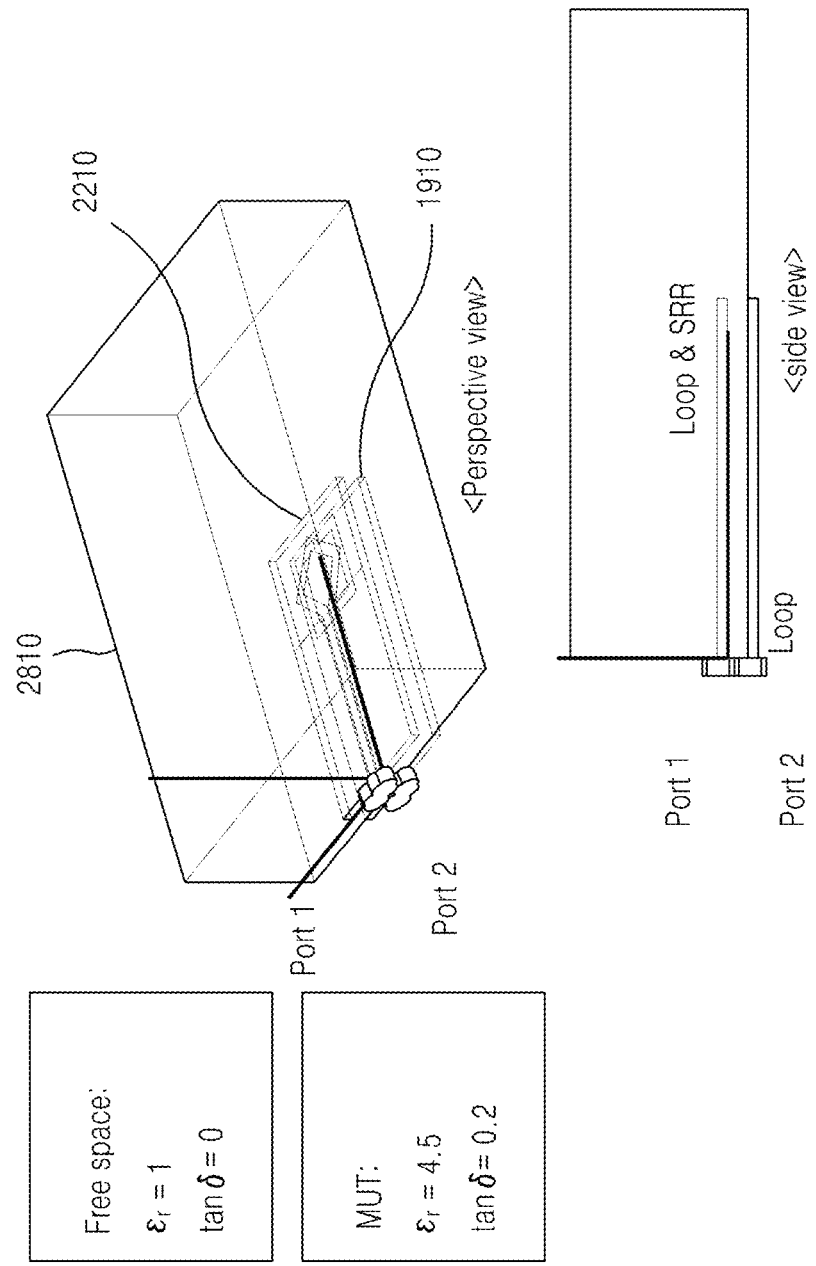
FIGS. 28 and 29 are diagrams illustrating a third example of frequency response experiments according to an embodiment of the present disclosure.
Figure 29:
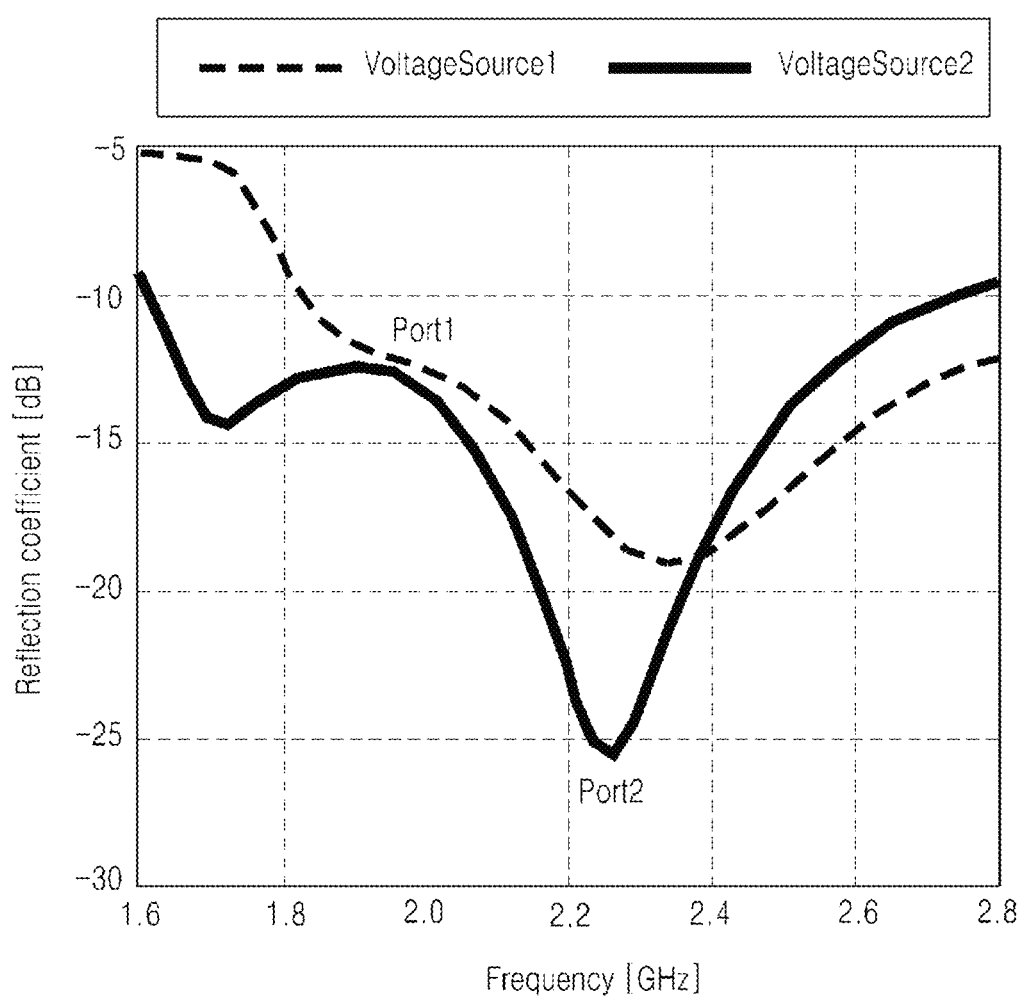

FIGS. 28 and 29 are diagrams illustrating a third example of frequency response experiments according to an embodiment of the present disclosure. FIG. 28 illustrates an example in which the sensor 2220 illustrated in FIGS. 22 and 23 was disposed within a MUT 2810, that is, a material having a specific dielectric constant, the first sensor 1910 was disposed outside the MUT 2810, and experiments were performed on frequency response characteristics. From a graph of FIG. 29, it may be seen that since one loop including the first sensor 1910 is present in a short-distance area outside the MUT 2810, frequency responses of two ports (port 1, 2) in a combined structure are not the same as those of a design in which the first sensor 1910 and the second sensor 1920 are separated from each other in the embodiments of FIGS. 25 and 26.

Figure 30:
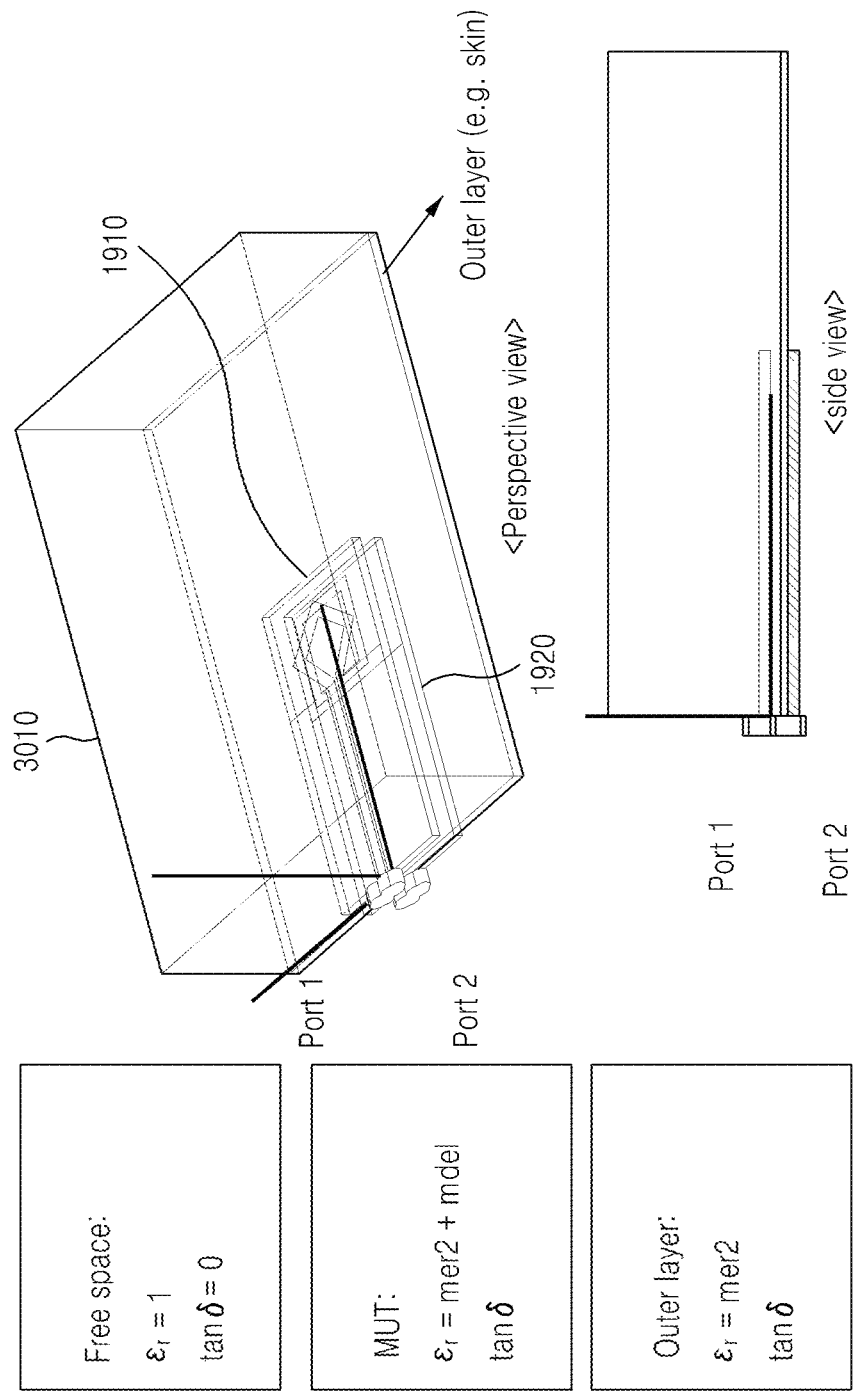
FIGS. 30 to 32 are diagrams illustrating a fourth example of frequency response experiments according to an embodiment of the present disclosure.
Figure 31:
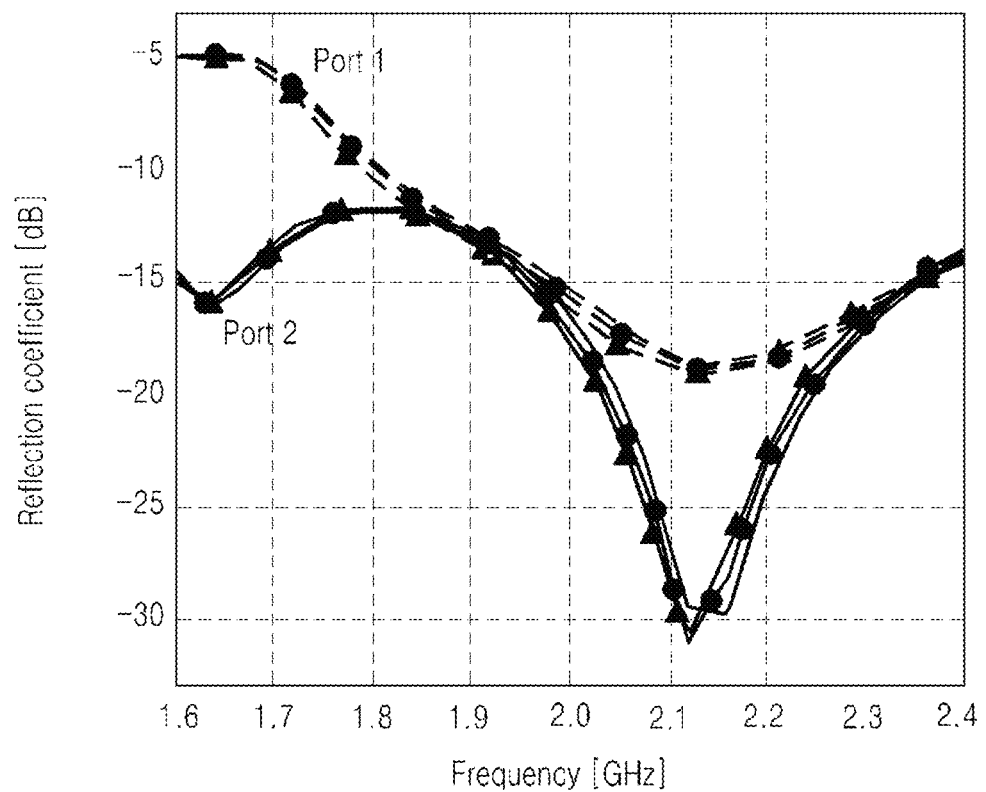
Figure 32:
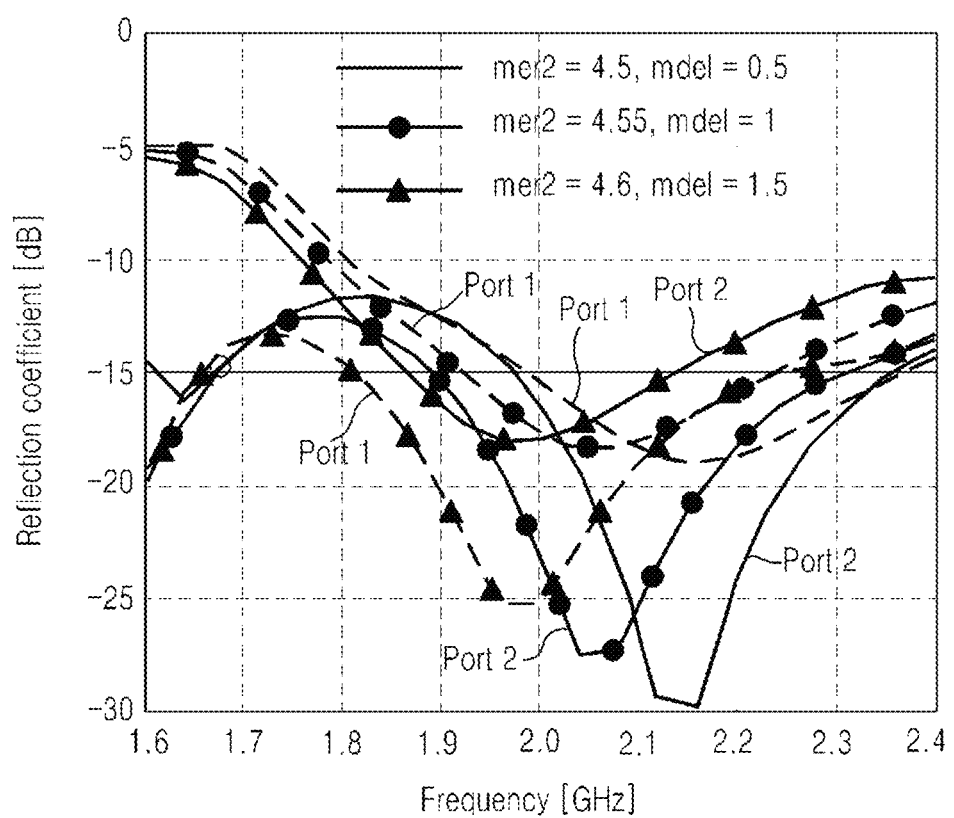

FIGS. 30 to 32 are diagrams illustrating a fourth example of frequency response experiments according to an embodiment of the present disclosure. FIG. 30 illustrates an example in which the first sensor 1910 was disposed within an MUT 3010, that is, a material having a specific dielectric constant, the second sensor 1920 was disposed outside the MUT 3010, an outer layer such as the skin was placed between the first sensor 1910 and the second sensor 1920, and experiments were performed on frequency response characteristics. In FIG. 30, "mer2" may indicate a dielectric constant of an outside part and in general, body) not affected by an analyte level, and "mdel" may indicate a difference between dielectric constants attributable to an analyte level. A graph of FIG. 31 illustrates frequency response characteristics in a port 1 and a port 2 when the dielectric constants "mer2" were 4.5, 4.55, and 4.6 and the difference "mdel" between the dielectric constants was 0.5. A desired responses is that both frequency responses of the two ports are changed when the dielectric constant "mer2" is changed (1) and that the frequency response of the port 2 is maintained and the frequency response of the port 1 is greatly changed when the difference "mdel" between the dielectric constants is changed (2). It may be seen that (1) is satisfied through the graph of FIG. 31. A graph of FIG. 32 illustrates an example in which both the dielectric constant "mer2" and the difference "mdel" between the dielectric constants were changed. FIG. 32 illustrates that when both the dielectric constant "mer2" and the difference "mdel" between the dielectric constants are changed, frequency responses of the port 1 and the port 2 are changed.

Figure 33:
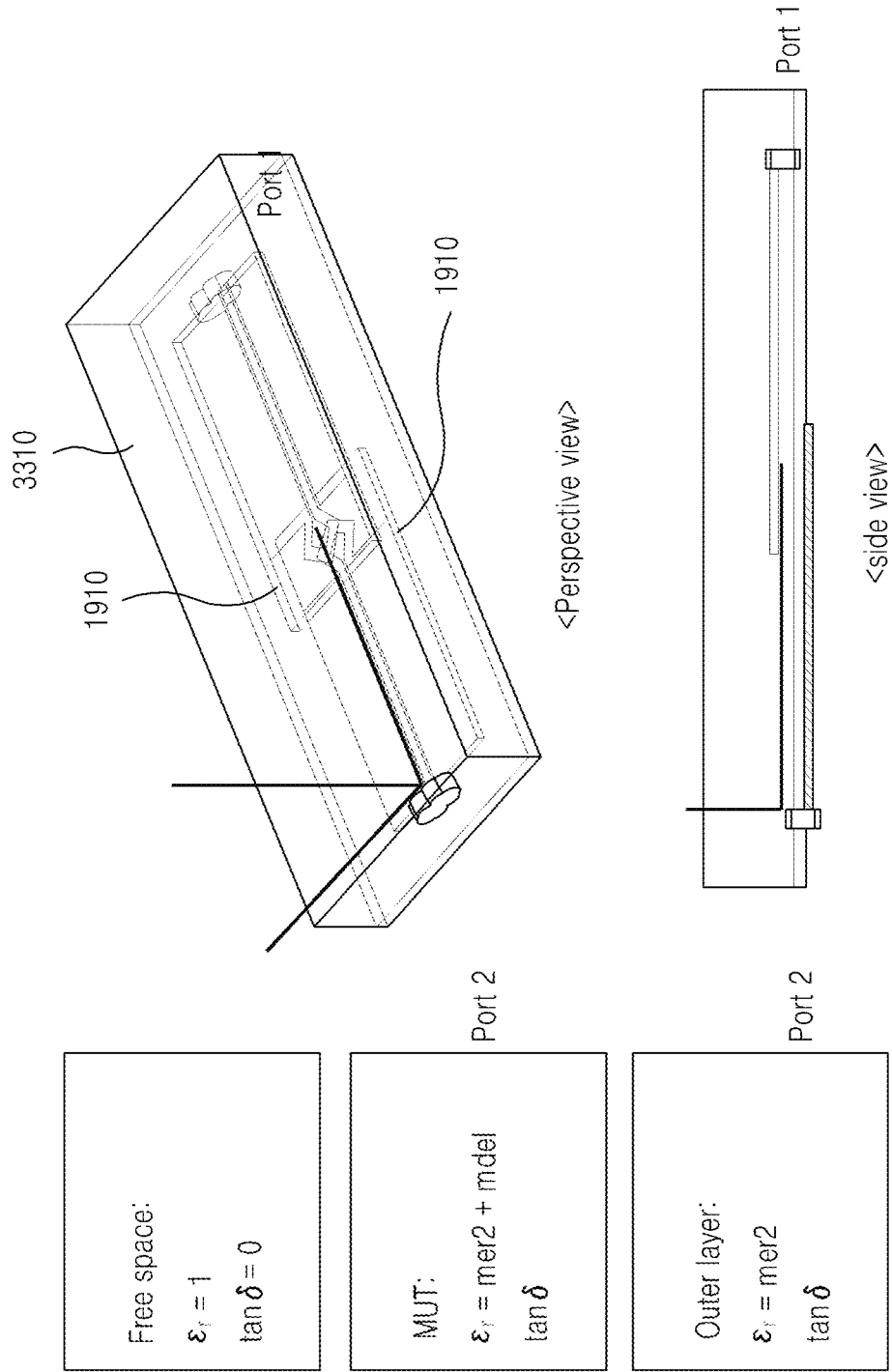
FIGS. 33 to 35 are diagrams illustrating a fifth example of frequency response experiments according to an embodiment of the present disclosure.
Figure 34:
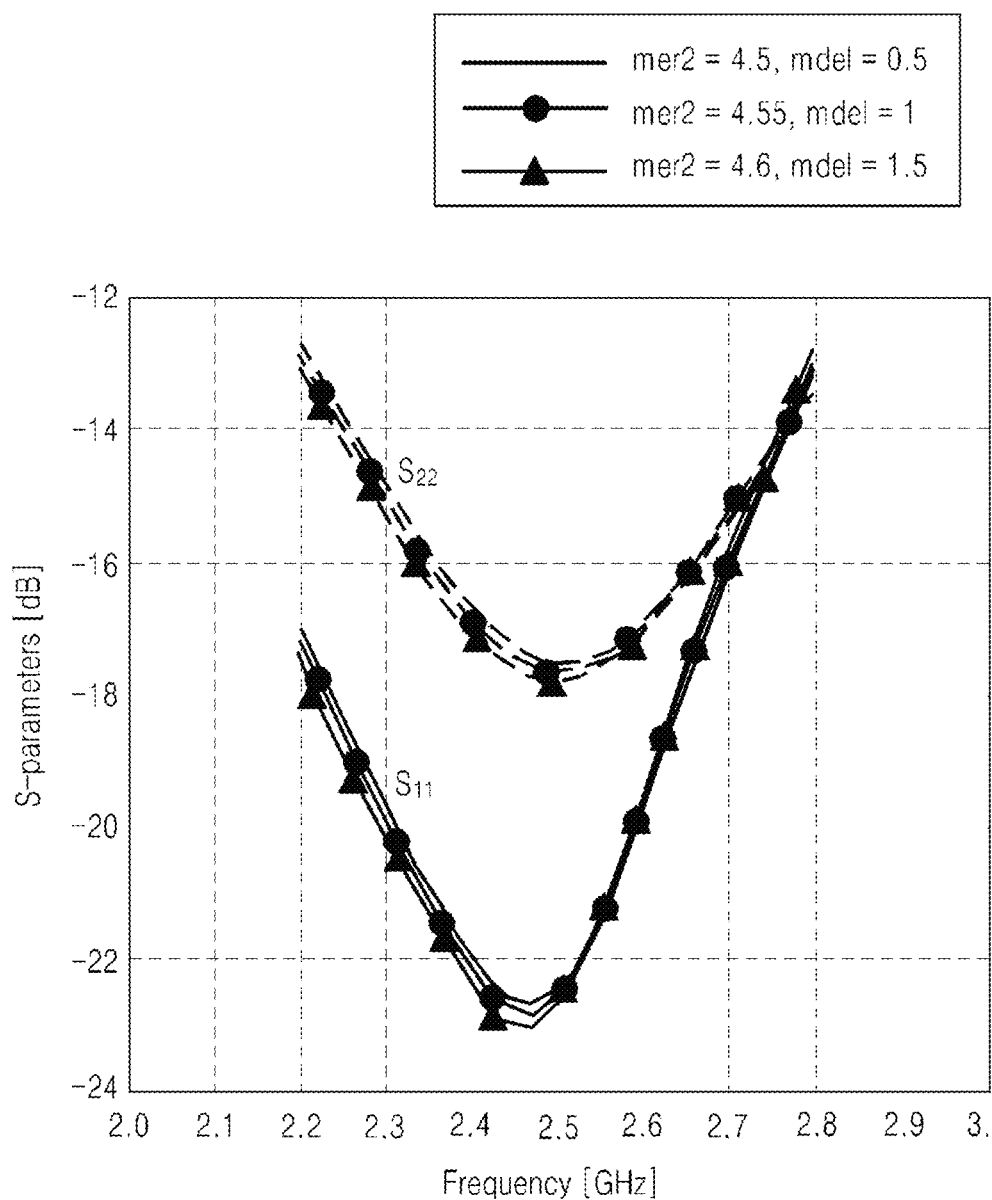
Figure 35:
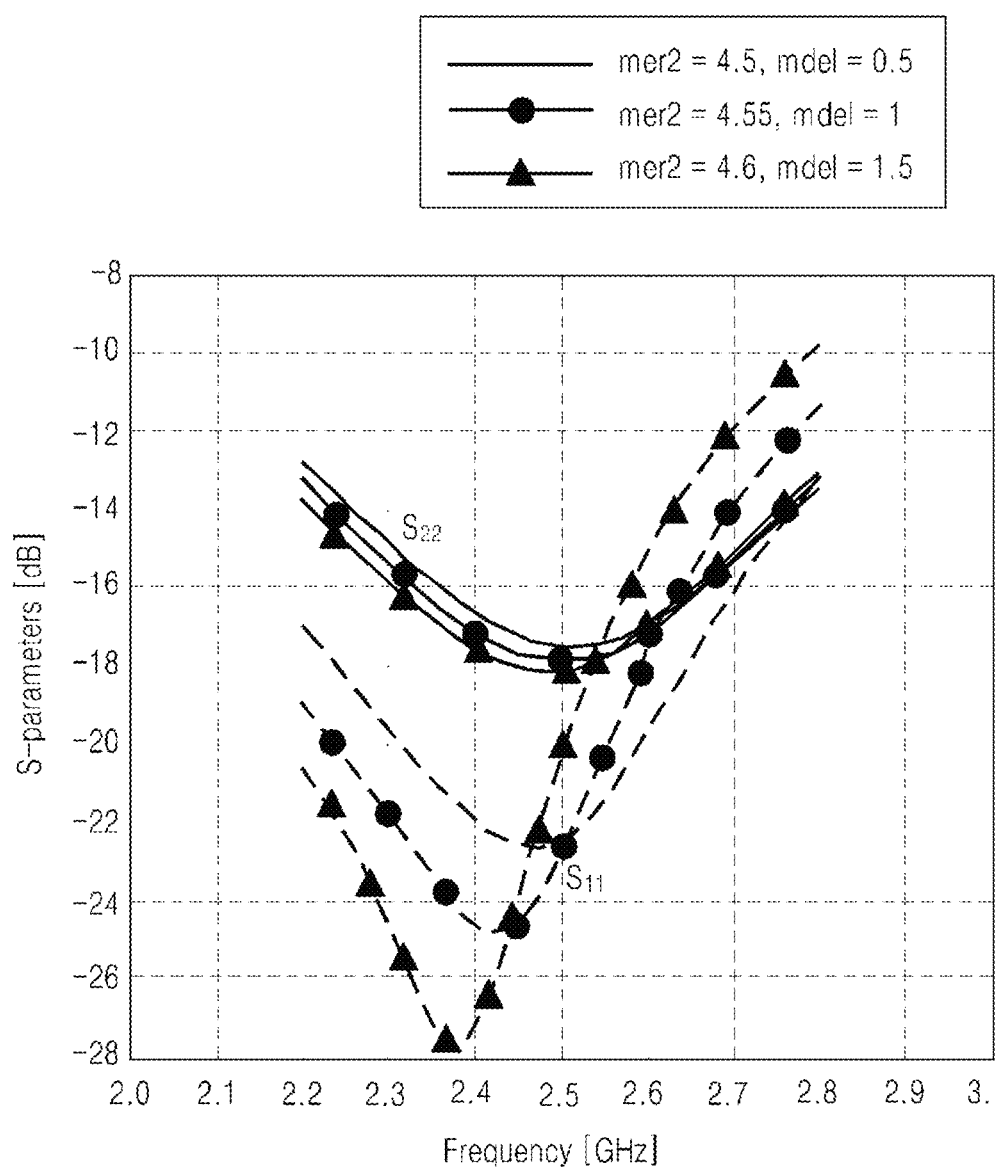

FIGS. 33 to 35 are diagrams illustrating a fifth example of frequency response experiments according to an embodiment of the present disclosure. FIG. 33 illustrates an example in which the first sensor 1910 was disposed within MUT 3310, that is, a material having a specific dielectric constant, the first sensor 1910 was disposed outside the MUT 3310, the first sensor 1910 within the MUT 3310 and the first sensor 1910 outside the MUT 3310 were disposed in opposite directions, and experiments were performed on frequency response characteristics. In this case, an outer layer, such as the skin, may be present between the first sensors 1910 disposed inside and outside the MUT 3310. FIGS. 33 and 34 illustrate scattering parameters $S_{11}$ and $S_{22}$ according to a change in a dielectric constant "mer2" and a difference "mdel" between the dielectric constants, respectively. If the other loop is present in a short-distance area of one loop, an unexpected frequency response may occur. A dummy loop may be replaced with a loop having a power source. The loop having a power source may perform two roles of sensing a surrounding environment and causing resonance in the other loop.

As described above, according to embodiments of the present disclosure, there can be provided the antenna device for measuring biometric information by using dark mode excitation and the implant device for measuring biometric information by using the antenna device.

The aforementioned system or device or apparatus may be implemented as a hardware component or a combination of a hardware component and a software component. For example, the device and component described in the embodiments may be implemented using a processor, a controller, an arithmetic logic unit (ALU), a digital signal processor, a microcomputer, a field programmable gate array (FPGA), a programmable logic unit (PLU), a microprocessor or one or more general-purpose computers or special-purpose computers, such as any other device capable of executing or responding to an instruction. The processing device may perform an operating system (OS) and one or more software applications executed on the OS. Furthermore, the processing device may access, store, manipulate, process and generate data in response to the execution of software. For convenience of understanding, one processing device has been illustrated as being used, but a person having ordinary skill in the art may understand that the processing device may include a plurality of processing elements and/or a plurality of types of processing elements. For example, the processing device may include a plurality of processors or a single processor and a single controller. Furthermore, a different processing configuration, such as a parallel processor, is also possible.

Software may include a computer program, a code, an instruction or a combination of one or more of them and may configure a processing device so that the processing device operates as desired or may instruct the processing devices independently or collectively. The software and/or the data may be embodied in any type of machine, a component, a physical device, a computer storage medium or a device in order to be interpreted by the processor or to provide an instruction or data to the processing device. The software may be distributed to computer systems connected over a network and may be stored or executed in a distributed manner. The software and the data may be stored in one or more computer-readable recording media.

The method according to embodiments may be implemented in the form of a program instruction executable by various computer means and stored in a computer-readable medium. The computer-readable medium may include a program instruction, a data file, and a data structure solely or in combination. The medium may continue to store a program executable by a computer or may temporarily store the program for execution or download. Furthermore, the medium may be various recording means or storage means having a form in which one or a plurality of pieces of hardware has been combined. The medium is not limited to a medium directly connected to a computer system, but may be one distributed over a network. An example of the medium may be one configured to store program instructions, including magnetic media such as a hard disk, a floppy disk and a magnetic tape, optical media such as a CD-ROM and a DVD, magneto-optical media such as a floptical disk, a ROM, a RAM, and a flash memory. Furthermore, other examples of the medium may include an app store in which apps are distributed, a site in which other various pieces of software are supplied or distributed, and recording media and/or storage media managed in a server. Examples of the program instruction may include machine-language code, such as a code written by a compiler, and a high-level language code executable by a computer using an interpreter.

As described above, although the embodiments have been described in connection with the limited embodiments and the drawings, those skilled in the art may modify and change the embodiments in various ways from the description. For example, proper results may be achieved although the aforementioned descriptions are performed in order different from that of the described method and/or the aforementioned components, such as the system, configuration, device, and circuit, are coupled or combined in a form different from that of the described method or replaced or substituted with other components or equivalents.

Accordingly, other implementations, other embodiments, and the equivalents of the claims fall within the scope of the claims.

The embodiments of the disclosure in which an exclusive property or privilege is claimed are defined as follows:

1. An antenna device comprising:
   an antenna configured to be disposed in a hypodermic area of a body;
   a power source connected to the antenna;
   a loop coupled to the antenna, wherein the loop is formed by a conducting wire, wherein a current is induced into the loop through an interaction with a magnetic field generated by the antenna, and wherein the magnetic field formed senses a biometric data;
   a sensor configured to collect one or more measurement data;
   a Bayesian filter-based algorithm configured to predict an analyte concentration;
   a processor communicatively coupled to the antenna and the sensor and configured to:
      receive the biometric data from the antenna;
      receive the one or more measurement data from the sensor;
      associate the biometric data and the one or more measurement data with the Bayesian filter-based algorithm; and
      predict an analyte concentration based on the biometric data and the one or more measurement data.

2. The antenna device of claim 1, wherein the loop further comprises an electric quadrupole moment.

3. The antenna device of claim 1, wherein the loop is a cross-shaped loop.

4. The antenna device of claim 1, wherein the loop has a length corresponding to half of a wavelength corresponding to a frequency of a supplied feeding signal.

5. The antenna device of claim 1, the antenna further comprising a dipole antenna, wherein the current is induced into the loop through an interaction between the loop and a magnetic field generated by an electric dipole moment of the dipole antenna.

6. The antenna device of claim 1, wherein the antenna connected to the power source comprises a loop antenna.

7. The antenna device of claim 1, wherein the antenna connected to the power source comprises a loop antenna using coplanar waveguide (CPW) feeding.

8. The antenna device of claim 1, wherein the loop comprises a parasitic loop connected to a power source different from the power source so that a current is induced in a direction opposite to a direction of a current flowing into the antenna connected to the power source.

9. The antenna device of claim 1, wherein the antenna device further comprises:
   an implant device configured to be inserted into a body having a target analyte, and
   an external device disposed outside the body having the target analyte, wherein the external device is implemented to radiate a magnetic field to the implant device configured to be inserted into the body having the target analyte through the antenna connected to the power source.

10. An implant system comprising:
    an implant device configured to be inserted into a hypodermic area of a body having a target analyte;
    an antenna device comprising a loop, wherein the loop is formed by a conducting wire,
    wherein a current is induced into the loop through an interaction with a magnetic field generated by the antenna, and wherein the magnetic field formed senses a biometric data;
    a sensor configured to collect one or more measurement data;
    an external device configured to be disposed outside the body, comprising:
       a Bayesian filter-based algorithm configured to predict an analyte concentration; and
       a processor communicatively coupled to the antenna and the sensor and configured to:
          receive the biometric data from the antenna;
          receive the one or more measurement data from the sensor;
          associate the biometric data and the one or more measurement data with the Bayesian filter-based algorithm; and
       predict an analyte concentration based on the biometric data and the one or more measurement data.

11. The implant system of claim 10, wherein
    the antenna is inside in the external device, and
    the external device is configured to radiate the magnetic field to the implant device through the antenna.

12. The implant system of claim 10, wherein the loop is configured to generate an electric quadrupole moment.

13. The implant system of claim 10, wherein the loop is cross-shaped.

14. The implant system of claim 10, wherein the loop has a length corresponding to half of a wavelength corresponding to a frequency of a supplied feeding signal.

15. The implant system of claim 10, the antenna further comprising a dipole antenna, wherein the current is induced into the loop through an interaction between the loop and a magnetic field generated by an electric dipole of the dipole antenna.

* * * * *